(12) United States Patent
Docherty et al.

(10) Patent No.: US 10,865,387 B2
(45) Date of Patent: Dec. 15, 2020

(54) METHODS OF OBTAINING PANCREATIC ENDOCRINE CELLS

(71) Applicant: The University Court of the University of Aberdeen, Aberdeen, Aberdeenshire (GB)

(72) Inventors: Kevin Docherty, Foresterhill Aberdeen (GB); Hilary Margaret Docherty, Foresterhill Aberdeen (GB); Maria Joao Marques De Lima, Foresterhill Aberdeen (GB); Kenneth Ross Muir, Foresterhill Aberdeen (GB); John Joseph Casey, Edinburgh (GB)

(73) Assignee: THE UNIVERSITY COURT OF THE UNIVERSITY OF ABERDEEN REGENT WALK, Aberdeen (GB)

( * ) Notice: Subject to any disclaimer, the term of this patent is extended or adjusted under 35 U.S.C. 154(b) by 732 days.

(21) Appl. No.: 15/310,490

(22) PCT Filed: May 14, 2015

(86) PCT No.: PCT/GB2015/051428
§ 371 (c)(1),
(2) Date: Nov. 11, 2016

(87) PCT Pub. No.: WO2015/173576
PCT Pub. Date: Nov. 19, 2015

(65) Prior Publication Data
US 2017/0073642 A1 Mar. 16, 2017

(30) Foreign Application Priority Data

May 14, 2014 (GB) .................................. 1408558.3
Jul. 28, 2014 (GB) .................................. 1413331.8

(51) Int. Cl.
*C12N 5/071* (2010.01)
*A61K 35/39* (2015.01)

(52) U.S. Cl.
CPC ............ *C12N 5/0676* (2013.01); *A61K 35/39* (2013.01); *C12N 2500/22* (2013.01); *C12N 2501/06* (2013.01); *C12N 2501/065* (2013.01); *C12N 2501/15* (2013.01); *C12N 2501/60* (2013.01); *C12N 2501/72* (2013.01); *C12N 2501/73* (2013.01); *C12N 2501/999* (2013.01); *C12N 2506/22* (2013.01); *C12N 2510/00* (2013.01)

(58) Field of Classification Search
CPC .................................................. C12N 5/0676
See application file for complete search history.

(56) References Cited

U.S. PATENT DOCUMENTS

2012/0039955 A1  2/2012  Xu

FOREIGN PATENT DOCUMENTS

| WO | 2009127719 A1 | 10/2009 |
| WO | 2011109837 A2 | 9/2011 |
| WO | 2014048788 A1 | 4/2014 |

OTHER PUBLICATIONS

Lima et al. (2013, Diabetes, vol. 62(8), pp. 2821-2833). (Year: 2013).*
Plath et al. (2011, Nat. Rev. Genet., vol. 12(4), pp. 253-265) (Year: 2011).*
Wang et al. (2019, Cell, vol. 27, pp. 3473-3485) (Year: 2019).*
Collombat et al.; "Opposing Actions of Arx and Pax4 in Endocrine Pancreas Development"; Genes & Development; pp. 2591-2603; (2003).
Collombat et al.; "The Simultaneous Loss of Arx and Pax4 Genes Promotes a Somatostatin-Producing Cell Fate Specification at the Expense of the Alpha- and Beta-cell Lineages in the Mouse Endocrine Pancreas"; Development; 132(13); pp. 2969-2980; (2005).
Courtney et al.; "The Inactivation of Arx in Pancreatic Altha-Cells Triggers Their Neogenesis and Conversion into Functional Beta-Like Cells"; PLoS Genet; 9(10); p. e1003934; (2013).
Dhawan et al.; "Pancreatic Beta Cell Identity Is Maintained by DNA Methylation-Mediated Repression of Arx"; Developmental Cell, Cell Press, US, 20(4); pp. 419-429; (2011).
International Search Report and Written Opinion; International Application No. PCT/GB2015/051428; International Filing Date May 14, 2015; dated Aug. 17, 2015; 12 pages.
Li et al.; "A Mesenchymal-to-Epithelial Transition Initiates and Is Required fr the Nuclear Reprogramming of Mouse Fibroblasts"; Cell Stem Cell, 7(1) pp. 51-63; (2010).
Lima et al.; "Suppression of Epithelial-to-Mesenchymal Transitioning Enhances Ex Vivo Reprogramming of Human Exocrine Pancreatic Tissue Toward Functional Insulin-Producing Beta-Like Cells"; Diabetes; 62(8); pp. 2821-2833 (2013).
Tiwari et al.; Klf4 Is a Transcriptional Regulator of Genes Critical for EMT, Including Njk1 (Mapk8); PLoS ONE; p. e57329; (2013).
Wilcox et al.; "Pancreatic Alpha-Cell Specific Deletion of Mouse Arx Leads to Alpha-Cell Identity Loss"; PLoS One; 8 (6); p. 366214; (2013).
Yoshiya et al.; "In Vitro Transdifferentiation of HepG2 Cells to Pancreatic-Like Cells by CCL4, D-Galactosamine, and ZnCl2"; Pancreas, Raven Press, New York, NY; 40(8); pp. 1245 and 1250-1251; (2011).
Zhang et al.; "Functional Role of an Islet Transcription Factor, INSM1/IA-1, on Pancreatic Acinar Cell Trans-Differention"; J Cell Physiol; 227(6); pp. 2470-2479; (2012).
Akinci et al.; "Reprogramming of Pancreatic Exocrine Cells Toward a Beta (B) Cell Character Using Pdx1, Ngn3 and MafA"; Biochem J.; 442; pp. 539-550; (2012).
Alipio et al.; "Reversal of Hyperglycemia in Diabetic Mouse Models Using Induced-Pluripotent Stem (iPS)-derived Pancreatic Beta-like Cells"; PNAS; 107(30); pp. 13426-13431; (2010).
Andersson et al.; "Survival of Isolated Human Islets of Langerhans Maintained in Tissue Culture"; The Journal of Clinical Investigation; 57; pp. 1295-1301; (1976).

(Continued)

*Primary Examiner* — Thaian N. Ton
*Assistant Examiner* — David A. Montanari
(74) *Attorney, Agent, or Firm* — Kilpatrick Townsend & Stockton LLP

(57) ABSTRACT

The present invention relates to methods of producing pancreatic endocrine cells and uses of the cells obtained using the methods. The method utilises inhibitors or combinations of factors to provide increased quantities of endocrine material, for example for transplantation purposes.

13 Claims, 16 Drawing Sheets

(56) References Cited

OTHER PUBLICATIONS

Figure 1:
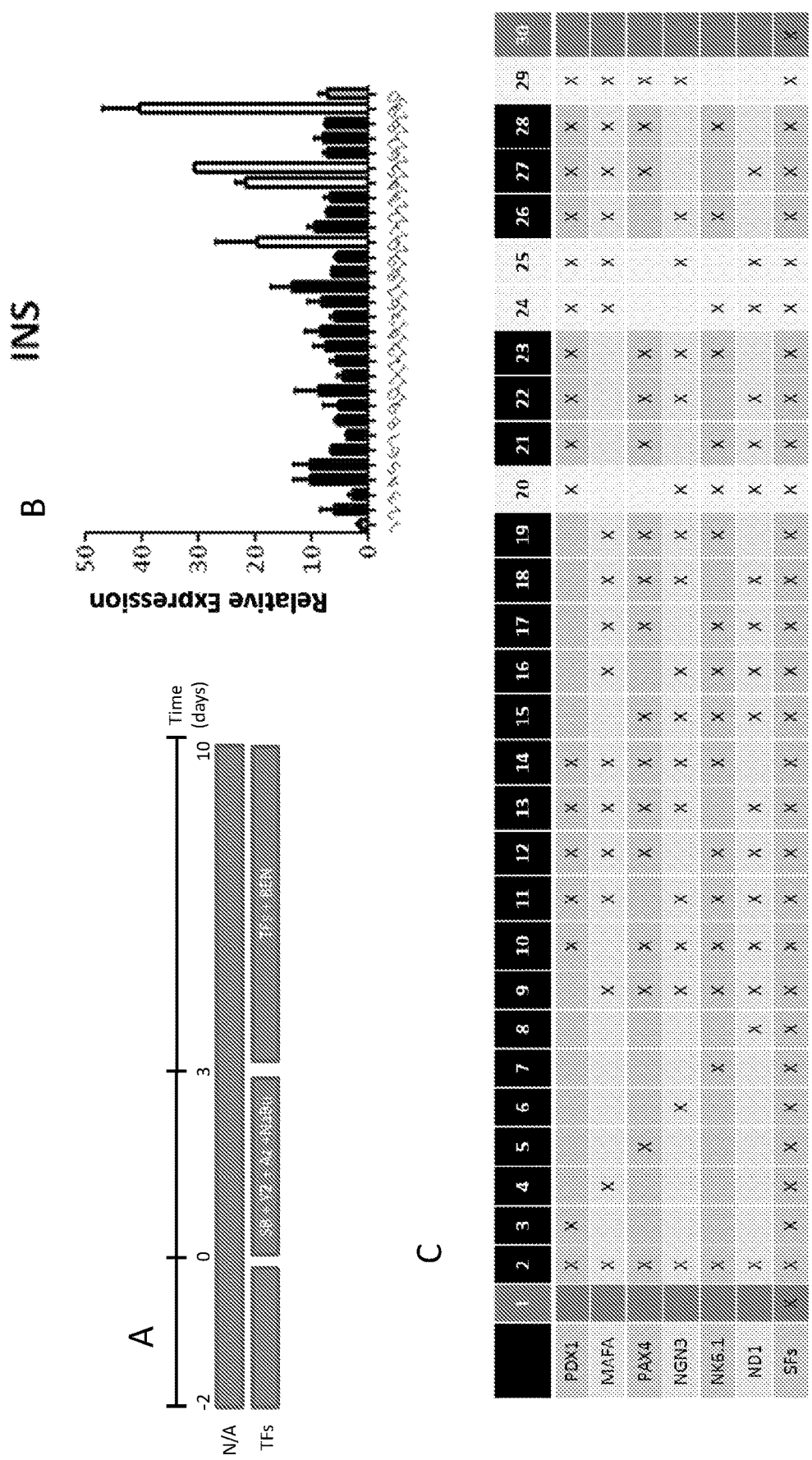

Ankrum et al.; "Mesenchymal Stem Cells: Immune Evasive, Not Immune Privilege"; Nat Biotechnol.; 32(3); pp. 252-260; (2014).
Baeyens et al; "In Vitro Generation of Insulin-producing Beta Cells from Adult Exocrine Pancreatic Cells"; Diabetologia; 48; pp. 49-57; (2005).
Bar et al.; "HES-1 Is Involved in Adaptation of Adult Human Beta-Cells to Proliferation In Vitro"; Diabetes; 57, pp. 2413-2420; (2008).
Bar et al.; "Redifferentiation of Expanded Human Pancreatic-Beta-Cell-derived Cells by Inhibition of the NOTCH Pathway"; Journal of Biological Chemistry; 287(21); pp. 17269-17280; (2012).
Bar et al.; "Redifferentiation of Expanded Human Pancreatic B-Cell-derived Cells by Inhibition of the NOTCH Pathway"; The Journal of Biological Chemistry; 287(21); pp. 17269-17280; (2012).
Beattie et al.; "Ex Vivo Expansion of Human Pancreatic Endocrine Cells"; Journal of Clinical Endocrinology and Metabolism; 82(6); pp. 1852-1856; (1997).
Birsoy et al.; "Transcriptional Regulation of Adipogenesis by KLF4"; Cell Metab.; 7(4); pp. 339-347; (2008).
Blum et al.; "Functional Beta-cells Maturation is Marked by an Increase in the Glucose Threshold for Insulin Secretion and by Expression of Urocortin3"; Nat Biotechnol;30(3); pp. 261-264; (2015).
Brodsky et al.; "The Requirement for Molecular Chaperones During Endoplasmic Reticulum-associated Protein Degradation Demonstrates That Protein Export and Import Are Mechanistically Distinct"; Journal of Biological Chemistry; 274(6); pp. 3453-3460; (1999).
Budd et al.; "Preproinsulin mRNA in the Rat Eye"; Investigative Ophthalmology & Visual Science; 34(2); pp. 463-469; (1993).
Chan et al.; "KLF4 and PBX1 Directly Regulate NANOG Expression in Human Embryonic Stem Cells"; Stem Cells; 27; pp. 2114-2125; (2009).
Chandra et al; "Islet-Like Cell Aggregates Generated from Human Adipose Tissue Derived Stem Cells Ameliorate Experimental Diabetes in Mice"; PLoS ONE; 6(6): 320615; 12 pages (2011).
Chase et al.; "Islet-Derived Fibroblast-Like Cells Are Not Derived Via Epithelial-Mesenchymal Transition From Pdx-1 or Insulin-Positive Cells"; Diabetes; 56; pp. 3-7; (2007).
Cho et al.; "Inhibition of Activin/nodal Signalling is Necessary for Pancreatic Differentiation of Human Pluripotent Stem Cells"; Diabetologia; 55; pp. 3284-3295; (2012).
Davani et al.; "Human Islet-Derived Precursor Cells Are Mesenchymal Stromal Cells That Differentiate and Mature to Hormone-Expressing Cells In Vivo"; Stem Cells; 25; pp. 3215-3222; (2007).
Gallo et al.; "Generation and Expansion of Multipotent Mesenchymal Progenitor Cells from Cultured Human Pancreatic Islets"; Cell Death and Differentiation; 14; pp. 1860-1871; (2007).
Houbracken et al.; "Lineage Tracing Evidence for Transdifferentiation of Acinar to Duct Cells and Plasticity of Human Pancreas"; Gastroenterology; 141;pp. 731-741; (2011).
Jiang et al.; "Generation of Insulin-Producing Islet-Like Clusters from Human Embryonic Stem Cells"; Stem Cells; 25; pp. 1940-1953; (2007).
Jiang et al.; "In Vitro Derivation of Functional Insulin-Producing Cells from Human Embryonic Stem Cells"; Cell Research; 17; pp. 333-344; (2007).
Karnieli et al.; "Generation of Insulin-Producing Cells from Human Bone Marrow Mesenchymal Stem Cells by Genetic Manipulation"; Stem Cells; 25; pp. 2837-2844; (2007).
Lee et al; "Expansion and Conversion of Human Pancreatic Ductal Cells Into Insulin-Secreting Endocrine Cells"; eLife 2013; 2:e00940; 22 pages; (2013); doi:10.7554/eLife.00940.
Lehembre et al.; "NCAM-induced Focal Adhesion Assembly: A Functional Switch Upon Loss of E-cadherin"; EMBO Journal; 27; pp. 2603-2615; (2008).

Lima et al.; "Pancreatic Transcription Factors Containing Protein Transduction Domains Drive Mouse Embryonic Stem Cells Towards Endocrine Pancreas"; PLos ONE; 7(5): e36481; 10 pages; (2012).
Lin et al.; "Kruppel-Like Factor 4, a Tumor Suppressor in Hepatocellular Carcinoma Cells Reverts Epithelial Mesenchymal Transition by Suppressing Slug Expression"; PLos ONE; 7(8) e43593; 13 pages (2012) doi:10.1371/journal.pone.0044593.
Liu et al.; "Critical and Reciprocal Regulation of KLF4 and SLUG in Transforming Growth Factor B-Initiated Prostate Cancer Epithelial-Mesenchymal Transition"; Molecular and Cellular Biology; pp. 941-953; (2012).
McCall et al.; "Update on Islet Transplantation"; Cold Spring Harb Perspect Med; 2:a007823; 16 pages; (2012).
Morton et al.; "Endocrine Precursor Cells from Mouse Isleets Are Not Generated by Epithelial-to-Mesenchymal Transition of Mature Beta Cells"; Mol Cell Endocrinol.; 270(1-2); pp. 87-93; (2007).
Muir et al.; "Cell Therapy for Type 1 Diabetes"; Q J Med; 107; pp. 253-259; (2014).
Ogihara et al.; "Combined Expression of Transcription Factors Induces AR42J-B13 Cells to Differentiate into Insulin Producing Cells"; Endocrine Journal; 55(4); pp. 691-698; (2008).
Ohgushi et al.; "Molecular Pathway and Cell State Responsible for Dissociation-Induced Apoptosis in Human Pluripotent Stem Cells"; Cell Stem Cell; 7; pp. 225-239; (2010).
Porat et al.; "Control of Pancreatic Beta Cell Regeneration by Glucose Metabolism"; Cell Metabolism; 13; pp. 440-449; (2011).
Rezania et al.; "Maturation of Human Embryonic Stem Cell-Derived Pancreatic Progenitors Into Functional Islets Capable of Treating Pre-existing Diabetes in Mice"; Diabetes; 61; pp. 2016-2029; (2012).
Rezania et al.; "Production of Functional Glucagon-Secreting alpha-Cells from Human Embryonic Stem Cells"; Diabetes; 60; pp. 239-247; (2011).
Rooman et al.; "Modulation of Rat Pancreatic Acinoductal Transdifferentiation and Expression of PDX-1 in Vitro"; Diabetologia; 43; pp. 907-914; (2000).
Russ et al.; "In Vitro Proliferation of Cells Derived From Adult Human B-Cells Revealed by Cell-Lineage Tracing"; Diabetes; 57; pp. 1575-1583; (2008).
Russ et al; "Epithelial-Mesenchymal Transition in Cells Expanded In Vitro From Lineage-Traced Adult Human Pancreatic Beta Cells"; PLOS One; 4(7); e6417; 8 pages (2009); doi:10.1371/journal.pone.0006417.
Ryan et al.; "Five-Year Follow-Up After Clinical Islet Transplantation"; Diabetes; 54; pp. 2060-2069; (2005).
Samavarchi-Tehrani et. al.; "Functional Genomics Reveals a BMP-Driven Mesenchymal-to-Epithelial Transition in the Initiation of Somatic Cell Reprogramming"; Cell Stem Cell; 7; pp. 64-77; (2010).
Schulz et al.; "A Scalable System for Production of Functional Pancreatic Progenitors from Human Embryonic Stem Cells"; PLos ONE; 7(5): e37004; 17 pages (2012); doi:10.1371/journal.pone.0037004.
Shapiro et al.; "Islet Transplantation in Seven Patients with Type 1 *Diabetes Mellitus* Using a Glucocorticoid-Free Immunosuppressive Regimen"; The New England Journal of Medicine; 343(4); pp. 230-238; (2000).
Skyler, J. S.; "Primary and Secondary Prevention of Type 1 Diabetes"; Diabet Med.; 30(2); pp. 161-169; (2013).
Swales et al.; "Plasticity of Adult Human Pancreatic Duct Cells by Neurogenin3-Mediated Reprogramming"; PLos ONE; 7(5); e-37055; 11 pages; (2012); doi:10.1371/journal.pone.0037055.
Takahashi et al.; "Induction of Pluripotent Stem Cells From Mouse Embryonic and Adult Fibroblast Cultures by Defined Factors"; Cell; 126; pp. 663-676; (2006).
Tateishi et al.; "Generation of Insulin-secreting Islet-like Clusters from Human Skin Fibroblasts"; Journal of Biological Chemistry; 383(46); pp. 31601-31607; (2008).
Weinberg et al.; "Lineage Tracing Evidence for In Vitro Dedifferentiation But Rare Proliferation of Mouse Pancreatic B-Cells"; Diabetes; 56; pp. 1299-1304; (2007).

(56) References Cited

OTHER PUBLICATIONS

White et al.; "Pluripotency-associated Stem Cell Marker Expression in Proliferative Cell Cultures Derived From Adult Human Pancreas"; Journal of Endocrinology; 211; pp. 169-176; (2011).

Yechoor et al.; "Neurogenin3 is Sufficient for in vivo Transdetermination of Hepatic Progenitor Cells into Islet-like Cells but not Transdifferentiation of Hepatocytes"; Dev Cell. 16(3); pp. 358-373; (2009).

Yori et al.; "Kruppel-like Factor 4 Inhibits Epithelial-to-Mesenchymal Transition Through Regulation of E-cadherin Gene Expression"; Journal of Biological Chemistry; 285(22); pp. 16854-16863; (2010).

Zanini et al.; "Differentiation of Mesenchymal Stem Cells Derived from Pancreatic Islets and Bone Marrow into Islet Like Cell Phenotype"; PLOS One; 6(12); e28175; 13 pages, doi:10.1371/journal.pone.0028175.

Zhang et al.; "Krkuppel-like Factor 4 (Klf4) Prevents Embryonic Stem (ES) Cell Differentiation by Regulating Nanog Gene Expression"; Journal of Biological Chemistry; 285(12); pp. 9180-9189; (2010).

United Kingdom Patent Application No. GB 1408558.3, Search Report dated Jul. 2, 2015, 4 pages.

Kordowich, S, et al., "Reprogramming into pancreatic endocrine cells based on developmental cues", Molecular and Cellular Endocrinology, 323(1): 62-69 (2010).

Cho, C H-H, et al., "Inhibition of activin/nodal signalling is necessary for pancreatic differentiation of human pluripotent stem cells", Apr. 30, 2012, pp. 3284-3295.

D'Amour, K A, et al., "Production of pancreatic hormone-expressing endocrine cells from human embryonic stem cells", Nature Biotechnology, 24(11), 2006, pp. 1392-1401.

Kroon, E, et al., "Pancreatic endoderm derived from human embryonic stem cells generates glucose-responsive insulin-secreting cells in vivo", Nature Biotechnology, 26(4), 2008, pp. 443-452.

Docherty, K, "Reprogramming Towards Pancreas β-Cells, Nuclear Reprogramming and Stem Cells", Stem Cell Biology and Regenerative Medicine, 2011, pp. 177-191.

Ferber, S, et al., "Pancreatic and duodenal homeobox gene 1 induces expression of insulin genes in liver and ameliorates streptozotocin-induced hyperglycemia", Nature Medicine, 6(5), 2000, pp. 568-572.

Kojima, H, et al., "NeuroD-betacellulin gene therapy induces islet neogenesis in the liver and reverses diabetes in mice", Nature Medicine, 9(5), 2003, pp. 596-603.

Wang, H-S, et al., "Transplantation of Insulin-Producing Cells Derived From Umbilical Cord Stromal Mesenchymal Stem Cells to Treat NOD Mice", Cell Transplantation, 20, 2011, pp. 455-466.

Zhou, Q, et al., "In vivo reprogramming of adult pancreatic exocrine cells to β-cells", Nature, 455, Oct. 2, 2008, pp. 627-632.

Lima, et al., "Efficient differentiation of AR42J cells towards insulin-producing cells using pancreatic transcription factors in combination with growth factors", Molecular & Cellular Endocrinology, 358(1), 2012, pp. 69-80.

International Application No. PCT/GB2015/051428, International Preliminary Report on Patentability dated Nov. 24, 2016, 9 pages.

Docherty, K, et al., "Embryonic stem cell therapy for diabetes mellitus", Semin Cell Dev Biol., 18(6), doi:10.1016/j.semcdb.2007.09.009, pp. 827-838, 2007.

Gershengorn, M C, et al., "Epithelial-to-mesenchymal transition generates proliferative human islet precursor cells", Science, 306, Dec. 24, 2004, pp. 2261-2264.

Hao, E, et al., "Beta-cell Differentiation From Nonendocrine Epithelial Cells of the Adult Human Pancreas", Nat. Med., 12(3), 2006, pp. 310-316.

Montgomery, A M P et al., "The Epithelial-to-Mesenchymal Transition of Human Pancreatic β-Cells: Inductive Mechanisms and Implications for the Cell-Based Therapy of Type I Diabetes", Curr. Diabetes Rev., 7(5), 2011, pp. 346-355.

Ouziel-Yahalom, L, et al., "Expansion and Redifferentiation of Adult Human Pancreatic Islet Cells", Biochem, Biophys. Res. Commun., 341(2), 2006, pp. 291-298.

\* cited by examiner

METHODS OF OBTAINING PANCREATIC ENDOCRINE CELLS

CROSS REFERENCE TO RELATED APPLICATIONS

This application is a National Stage Application of PCT/GB2015/051428, filed May 14, 2015, which claims the benefit of priority to GB Application No. 1408558.3 filed on May 14, 2014 and GB Application No. 1413331.8 filed on Jul. 28, 2014, both of which are incorporated by reference in their entirety herein.

TECHNICAL FIELD

The present invention relates to methods of producing pancreatic endocrine cells and uses of the cells obtained using the methods.

BACKGROUND ART

Diabetes is now recognized as a global epidemic that affects around 6% of the world's adult population. The International Diabetes Foundation Global Atlas predicts that the numbers will increase from 366 million in 2011 to 552 million in 2030.

There are two main forms of the disease; type 1 diabetes (T1D) and type 2 diabetes (T2D). Both are associated with decreased numbers of insulin secreting β-cells in the islets of Langerhans.

T1D is an autoimmune disorder in which activated CD4+ and CD8+ T lymphocytes infiltrate the islets and selectively destroy the β-cells. Although its onset is usually during infancy and puberty, it can occur at any age. The destruction of β-cells is initiated three or four years before the symptoms develop such that at the time of presentation up to 70-80% of the β-cell mass is lost through apoptosis. T1D accounts for 5-10% of diabetes cases.

T2D results from a combination of insulin resistance and β-cell failure and is normally associated with being overweight or obese. It is particularly difficult to treat since the impaired actions of insulin lead to elevated blood levels of glucose and fatty acids, which in turn affect the function of the β-cell and in time, through inflammatory mechanisms, increase β-cell apoptosis. Very much a disease of middle-aged or elderly people, there has been an inexorable decrease in the age of onset of T2D associated with an increase in childhood obesity.

In the case of T1D, it is hoped that a cure may come from immune interventions directed at preventing the disease prior to the establishment of autoimmunity (Thrower and Bingley, 2011). Although several immunotherapeutic targets have been identified, there are still major challenges in setting up and evaluating vaccine trials (Skyler, 2013).

In the meantime improved insulin therapy, with emphasis on closed loop delivery systems or islet transplantation, is generally accepted as the best way forward. A comparison of continuous glucose monitoring data from patients on closed loop delivery systems and those that have undergone islet transplants indicates that closed loop delivery systems cannot get close to matching the control or consistently restore awareness of hypoglycaemia that can be achieved by islet transplantation.

Islet transplantation, mainly in the context of syngeneic transplantation following removal of the pancreas in patients with pancreatitis has been around since the early 1990's (McCall and Shapiro, 2012). The success rate for syngeneic islet transplants has been relatively good, but allogeneic transplantation of donor islets for the treatment of T1D was plagued from the outset with poor success rates; 8% graft function after one year. This changed with the introduction of the Edmonton Protocol in 2000, which placed emphasis on transplanting a sufficiently large number of islets, minimizing the cold ischemia time and changing the immunosuppressive region and in particular avoiding the use of steroids that are known to affect islet cell function (Shapiro et al., 2000).

Since the establishment of the Edmonton protocol, islet transplantation has become an effective and viable therapeutic option for Type 1 diabetes. Islet transplantation is accepted as the best alternative treatment to insulin for type 1 diabetes due to the low risk of hypoglycemic unawareness. However islet transplantation typically requires multiple donors to achieve insulin independence (Shapiro et al., 2000).

The shortage of donor islets has driven research towards new sources of insulin producing cells and replenishable supplies of islets for transplantation.

Several potential strategies exist for developing a replenishable supply of β-cells. One of these is through directed differentiation of human embryonic stem cells (hESCs) or induced pluripotent stem cells (iPSCs) towards a β-cell lineage, through an attempt to mimic the signalling pathways that are triggered during pancreatic development (Al-ipio et al., 2010; Blum et al., 2012; Cho, et al., 2012; D'Amour et al., 2006; Jiang et al., 2007; Jiang et al., 2007; Kroon et al., 2008; Rezania et al., 2011; Rezania et al., 2012; Schulz et al., 2012; Tateishi et al., 2008).

Another strategy involves transdifferentiating or reprogramming one fully differentiated adult cell type to another (Docherty, 2011). Thus, insulin-producing cells can be generated from liver (Ferber et al., 2000; Kojima et al., 2003; Yechoor et al., 2009), bone marrow (Karnieli et al., 2007) adipose tissue (Chandra et al., 2011) and cells derived from the umbilical cord (Wang et al., 2011).

Murine pancreatic exocrine cells can be reprogrammed (Ogihara et al., 2008) in vivo and in vitro towards insulin-producing cells that are phenotypically similar to β-cells. Most of the strategies applied to murine models involved the exogenous expression of pancreatic transcription factors that are important for normal endocrine pancreatic development (Akinci et al., 2012; Lima et al., 2012). Although expression of the three transcription factors PDX1, NGN3 and MAFA in exocrine cells of murine pancreas resulted in transdifferentiation of these cells towards the β-cell lineage in vivo (Zhou et al., 2008), the same transcription factors were unable to generate functional β-cells in vitro (Akinci et al., 2012) and further studies have shown that additional transcription factors such as NKX6.1, PAX4 or IA-1 (Akinci et al., 2012; Lima et al., 2012; Ogihara et al., 2008) and growth factors such as betacellulin, TGF-β and EGF (Baeyens et al., 2005; Zhang et al., 2012) may be important for generating functional transdifferentiated β-cells in vitro.

It has previously been described (Lima et al., 2013) how cells of the adult human exocrine pancreas obtained from the islet isolation procedure can be reprogrammed towards functional β-like cells in vitro. When placed in culture the acinar cells undergo epithelial-mesenchymal transitions (EMT), as demonstrated by genetic lineage tracing, to form a monolayer of mesenchymal cells. Efficient reprogramming was achieved using forced expression of four pancreatic transcription factors (PDX1, NGN3, PAX4 and MAFA) followed by culture with the growth factors betacellulin, exendin-4, the vitamin nicotinamide and small molecules that facilitate DNA binding of transcription factors.

It was shown that protocol generates predominantly glucagon positive cells, which responded to glucose in a manner similar to that of pancreatic α-cells in vitro and in vivo. These studies demonstrated that reprogramming of pancreatic exocrine cells towards functional insulin producing cells could be further enhanced by suppressing EMT using inhibitors of TGF-β1 and Rho-kinase signalling pathways. The resultant cells secreted insulin in response to glucose and successfully prevented the onset of diabetes when grafted in a streptozotocin diabetic mouse model. However, cells reprogrammed using methods in Lima et al. 2013 express only 1% of the insulin levels found in mature adult islets.

Nevertheless it can be seen that novel methods of providing endocrine (islet) materials, including (but not limited to) insulin secreting β-cells, would provide a contribution to the art.

DISCLOSURE OF THE INVENTION

The present invention provides, inter alia methods, uses and kits for obtaining pancreatic endocrine cells. The invention thus has utility, inter alia, for providing increased quantities of endocrine material for use in transplantation.

As described in more detail in the Examples below, the present inventors have shown, unexpectedly that inhibiting ARX can enhance reprogramming of human exocrine-derived cells to beta-cells in the presence of PAX4. The Examples suggest that the regulatory loop between ARX and PAX4 during the final stages of pancreatic development is essential for the glucose-sensitive functionality of human beta cells generated in vitro.

The inventors have shown for the first time that inhibition of ARX, along with PAX4 overexpression, is crucial for the transdifferentiation of human exocrine cells towards mature, glucose responsive beta-like cells that have the potential to be used in future cell therapy for type 1 diabetes.

The present inventors show that the cells produced by the protocols in Lima et al. (2013) express only 1% of the insulin levels found in mature adult islets. By contrast, beta-like cells produced using methods described herein were shown to be able to produce insulin at a much higher level, about 15% of adult human cells.

Without being limited to a particular theory, the present inventors suggest that the difference in insulin expression observed between mature islets and transdifferentiated/reprogrammed cells as produced in Lima et al. may be because the latter had not reached the same maturation status as adult islets.

The present inventors have also identified combinations of transcription factors that promote reprogramming to other endocrine cells including alpha and delta cells.

It has previously been shown in the developing mouse pancreas that the interplay between the transcription factors PAX4 and ARX plays a pivotal role in the final maturation of the beta and alpha cell lineages (Collombat et al. 2003). The beta cell lineage is established (in part) due to the inhibition of ARX by PAX4 (Collombat et al. 2003).

The present invention provides methods of obtaining pancreatic endocrine cells by reprogramming starting cells, for example pancreatic cells such as cells from an exocrine enriched fraction. In the context of the present invention, methods of reprogramming may also be referred to as methods of transdifferentiating cells.

The invention relates generally to methods for ex-vivo reprogramming comprising:
 a) providing pancreatic cells to be reprogrammed,
 b) reprogramming the cells, wherein the reprogramming comprises treating the cells with one or more transcription factors,
 c) thereby obtaining pancreatic endocrine cells.

Thus the invention relates generally to methods for ex-vivo reprogramming of pancreatic cells to form endocrine cells, the method comprising treating the cells with one or more transcription factors.

The invention generally provides methods for obtaining a population of pancreatic endocrine cells comprising:
 a) providing pancreatic cells to be reprogrammed,
 b) reprogramming the cells, wherein the reprogramming comprises treating the cells with one or more transcription factors,
 c) thereby obtaining an pancreatic endocrine cell.

The transcription factors comprise one or more of: PAX4, PDX1, MAFA, NGN3, NKX6.1, ND1.

In the methods of the invention, combinations of transcription factors and suitable culture conditions (including appropriate inhibitors, substrates and glucose concentrations) may be used in order to direct treated cells along a particular lineage, or favour a particular outcome, thereby permitting the generation of various types of epithelial cells of the pancreas. Selected transcription factors may also be inhibited to likewise direct the treated cells along a particular lineage.

In one aspect of the invention the cells obtained are beta-like cells.

The invention provides a method for ex-vivo reprogramming comprising:
 a) providing pancreatic cells to be reprogrammed
 b) reprogramming the cells, wherein the reprogramming comprises:
  (i) treating the cell with one or more transcription factors comprising PAX4, and
  (ii) inhibiting ARX expression and/or function,
 c) thereby obtaining a beta-like cell.

The invention provides a method for ex-vivo reprogramming of pancreatic cells to form beta-like cells, the method comprising:
 a) treating the cell with one or more transcription factors including PAX4; and
 b) inhibiting ARX expression and/or function.

The invention provides a method for obtaining a population of beta-like cells, the method comprising:
 a) providing pancreatic cells to be reprogrammed
 b) reprogramming the cells, wherein the reprogramming comprises:
  (i) treating the cell with one or more transcription factors comprising PAX4, and
  (ii) inhibiting ARX expression and/or function,
 c) thereby obtaining a beta-like cell.

In the methods for obtaining beta-like cells, the transcription factors may comprise PDX1, NGN3 and MAFA.

In preferred embodiments the invention relates to methods of ex-vivo reprogramming of human pancreatic exocrine cells towards functional insulin-secreting beta cells, comprising treating the cells with PAX4, inhibiting ARX, wherein the cells are cultured in low glucose and on laminin.

The present invention also relates to the use of ARX inhibitors to enhance reprogramming of pancreatic cells (e.g. exocrine cells) toward beta-like cells. Use of an ARX inhibitor may be in conjunction with the conditions, including factors and agents that are used in the methods of reprogramming described herein. An ARX inhibitor may inhibit the expression and/or function of ARX.

In some embodiments the cells are treated with zinc to enhance reprogramming.

The invention also provides methods of reprogramming pancreatic cells to obtain alpha-like cells that express glucagon mRNA. In such methods, the reprogramming may comprise treating the cell with transcription factors including one of the following combinations:
  (i) PDX1, MAFA, PAX4 and NKX6.1;
  (ii) PDX1, PAX4, NGN3 and NKX6.1;
  (iii) MAFA, PAX4, NGN3 and NKX6.1;
  (iv) MAFA, PAX4, NGN3 and NKX6.1, ND1;
  (v) MAFA.

The invention also provides methods of reprogramming pancreatic cells to obtain delta-like cells that express somatostatin mRNA. In such methods, the reprogramming may comprise treating the cell with transcription factors including one of the following combinations:
  (i) PDX1, MAFA, PAX4 and ND1;
  (ii) PDX1, MAFA, NGN3 and ND1;
  (iii) MAFA, PAX4, NGN3 and NKX6.1, ND1;
  (iv) MAFA, Example Starting Materials The invention generally provides methods of reprogramming appropriate cell populations towards a pancreatic cell phenotype, particularly a pancreatic endocrine cell phenotype. The starting cell population may be pluripotent stem cells, or other stem or progenitor cells, but as is described in more detail in the Examples, the present inventors have shown in particular that pancreatic cells exocrine cells can be reprogrammed toward pancreatic endocrine cells. Preferably the cells are exocrine cells.

Although the cells may be any mammalian cells (e.g. primate, rodent, porcine, bovine, canine, equine, feline, and so on) preferably the cells for use in methods the present invention are human pancreatic cells, for example epithelial cells. In preferred embodiment the cells for use in the methods of the present invention comprise pancreatic exocrine cells. Exocrine cells for use in the present invention can be obtained, for example from human donor pancreases.

A preferred starting material is an exocrine enriched fraction (EEF) of the pancreas. The EEF may be a by-product of islet isolation procedure, for example that used in the Edmonton protocol. The EEF may be obtained by a method involving digesting the pancreatic tissue with collagenase, and then by a step of centrifugation, leading to an islet enriched fraction and the exocrine enriched fraction.

The pancreatic starting material may include ductal cells. Cells may be passaged or otherwise expanded prior to use.

The starting cell population is cultured ex-vivo in conditions described herein to carry out the methods of the invention.

Example Product Material

As described above, methods disclosed herein may obtain endocrine cells, for example including beta-like cells that express insulin mRNA. Beta-like cells have some properties of endogenous beta cells (β-cells) and can be identified using markers of beta-cells such as insulin mRNA expression or protein production. ELISA may be used to monitor insulin protein production. Insulin production can be monitored by monitoring C-peptide production.

Accordingly, in some embodiments the cells obtained in using the methods of the invention are beta-like cells that express insulin mRNA. In preferred embodiments, the beta-like cells are capable of producing insulin protein in response to glucose stimulation. In some embodiments the beta-like cells obtained express insulin at a level of at least 5% of that in adult human islets. For example, the cells obtained may produce insulin at a level of at least 5%, 6%, 7%, 8%, 9%, 10%, 11%, 12%, 13%, 14%, 15%, 16%, 17%, 18%, 19%, 20%, 25% or 30% of that in adult human islets in the same conditions.

In some embodiments the beta-like cells obtained in the methods produce C-peptide in response to glucose stimulation.

The beta-like cells obtained may produce C-peptide at a level of at least 5%, 10% or 15% of that in adult human islets. For example, the cells obtained may produce C-peptide at a level of at least 5%, 6%, 7%, 8%, 9%, 10%, 11%, 12%, 13%, 14%, 15%, 16%, 17%, 18%, 19%, 20%, 25% or 30% of that in adult human islets in the same conditions.

In some embodiments methods described herein can be used to obtain alpha-like cells that express glucagon mRNA. Alpha-like cells may also express glucagon protein.

In some embodiments methods described herein can be used to obtain delta-like cells that express somatostatin mRNA. Delta-like cells may express somatostatin protein.

Other markers that indicate differentiation (and reprogramming) in the context of the present invention include endogenous expression of endocrine expression factors such as NGN3, MAFA, NKX6.1 and ND1, and expression of epithelial markers such as E-cadherin and EPCAM. Additionally cells may undergo a morphological transition to a more rounded epithelial form. Cells obtained by methods of the present invention may have one or more of these markers, or other markers associated with the desired cell product.

Some embodiments and aspects of the present invention will now be discussed in more detail. Any sub-titles herein are included for convenience only, and are not to be construed as limiting the disclosure in any way.

Use of Transcription Factors

In the methods, treatment to reprogram the cell comprises treatment with one or more reprogramming transcription factors. The cells may be cultured in the presence of the (exogenous) transcription factors for 3-10 days, for example, 4-9 days or 5-8 days. The cells may be cultured with the transcription factors for 7 days for example.

In the methods of the invention, treatment with transcription factors may involve introducing a nucleic acid or protein preparation which expresses or provides one or more of the transcription factors into the cells.

In the methods, treating the cells may involve culturing the cells in the presence of a protein preparation of one or more transcription factors in combinations described herein. Where the methods involve culturing the cells with protein preparations, the culturing allows the differentiation modulating factors to be taken up by the cell.

In alternative embodiments treating the cells with one or more transcription factors involves expressing the transcription factors in the cells. Examples of suitable expression vectors for this purpose are discussed in more detail hereinafter.

In some embodiments of the method, treating the cells with one or more transcription factors involves contacting the cells with a protein preparation of the transcription factors.

The expressions 'culturing the cells in the presence of . . . ', 'culturing the cells in media comprising . . . ', 'treating cells with . . . ', 'contacting the cells with' and 'introducing . . . into the cell' are used interchangeably, unless context demands otherwise.

The expressions 'expressing . . . in the cell' are used interchangeably with 'introducing a nucleic acid which expresses . . . ' in method steps of the present invention, unless context demands otherwise.

The transcription factors include one or more transcription factors selected from: PDX1, MAFA, PAX4, NGN3, NKX6.1 and NeuroD1 (ND1). In preferred embodiments human transcription factors are used.

Details of the human transcription factors and their protein and nucleotide sequences can be found as indicated:

| Transcription Factor | Uniprot accession number | version | Genbank accession number and version |
|---|---|---|---|
| PDX1 | P52945 | 143 | NM_000209.3 |
| MAFA | Q8NHW3 | 87 | NM_201589.3 |
| PAX4 | O43316 | 137 | NM_006193.2 |
| NGN3 | Q9Y4Z2 | 108 | NM_020999.3 |
| NKX6.1 | P78426 | 116 | NM_006168.2 |
| ND1 | Q13562 | 143 | NM_002500.4 |

Different transcription factors of combinations of transcription factors are preferable depending on the type of cells that are wanted from the methods.

Production of Beta-Like Cells

Where the methods are used to obtain beta-like cells, the pancreatic cells are treated with, at least, PAX4.

Preferred combinations of transcription factors for use in treating pancreatic cells in methods for obtaining beta-like cells include combinations comprising: PDX1, MAFA, NGN3 and PAX4 (condition 29).

Most preferred is a combination of transcription factors consisting of or consisting essentially of: PDX1, MAFA, NGN3 and PAX4 (condition 29). In some embodiments of the methods for obtaining beta-like cells, the transcription factors comprise PDX1, MAFA, NGN3 and PAX4, but do not comprise NKX6.1 and/or ND1.

Inhibition of ARX

The Examples show for the first time that inhibition of ARX, along with PAX4 overexpression, is crucial for the transdifferentiation of human exocrine cells towards mature, glucose responsive beta-like cells.

Accordingly, in methods of the present invention reprogramming the cells may comprise inhibition of ARX expression and/or function, combined with treatment of the cells with PAX4. Preferably the cells are also treated with transcription factors comprising, consisting or consisting essentially of: PDX1, MAFA, NGN3 and PAX4 (condition 29). Details of the human ARX and its protein and nucleotide sequences can be found at Uniprot (Accession number: Q96QS3 (version 120)) and Genbank (accession number and version: NM_139058.2).

Inhibition of ARX expression and/or function may comprise inhibition of: transcription of the gene, RNA maturation, RNA translation, post-translational modification of the protein, binding of the protein to a target. Inhibition may be conducted by an inhibitor that is a nucleic acid, a polypeptide, a protein, a peptide or a chemical compound. The term "expression" when used in the context of expression of a gene or nucleic acid refers to the conversion of the information, contained in a gene, into a gene product. A gene product can be the direct transcriptional product of a gene (e.g., mRNA) or a protein produced by translation of a mRNA. Gene products include messenger RNAs which are modified, by processes such as capping, polyadenylation, methylation, and editing, and proteins (e.g., ARX) modified by, for example, methylation, acetylation, phosphorylation, ubiquitination, SUMOylation, ADP-ribosylation, myristilation, and glycosylation. Inhibition of ARX expression may be by using antisense nucleic acid capable of inhibiting transcription, or translation of the corresponding messenger RNA. The antisense nucleic acid can comprise all or part of the sequence of ARX, or of a sequence that is complementary thereto. The antisense sequence can be a DNA, and RNA (e.g. siRNA) or a ribozyme. In a preferred embodiment ARX expression is inhibited by small inhibitory RNA (siRNA). Nucleic acids including RNAs can be transduced into the cells using vectors, such as viral vectors.

Methods of inhibiting ARX expression are discussed in more detail hereinafter.

Inhibition of ARX may be carried out during treatment with the transcription factor(s). Inhibition of ARX may be carried out at the late stages of the reprogramming method. For example, inhibition of ARX may be carried out at 0-1, 1-2, 2-3, 3-4 or 4-5 days after treatment with the transcription factor(s) begins. For example about 1, 2, 3, 4, or 5 days after treatment with the transcription factor(s) begins. Inhibition of ARX may be carried out about 3 days after treatment with the transcription factor(s) begins. In some embodiments inhibition of ARX may be carried out about 4, 5, 6 or 7 days after the start of the reprogramming step, for example 6 days after the start of the reprogramming step.

Treatment with Zinc

The present inventors have shown that treatment of the cells with zinc increases both the level of insulin mRNA expression and the C-peptide content of the cells in the reprogramming methods of the invention.

Accordingly, in preferred embodiments the cells are treated with zinc. For example the cells may be treated with $ZnCl_2$.

Zinc (e.g. $ZnCl_2$) may be added at a concentration of about 0.1 μM to about 100 μM, for example from about 1 μM to about 20 μM, about 5 μM to about 15 μM, about 8 μM to about 12 μM. Preferably zinc (e.g. $ZnCl_2$) is added at a concentration of about 10 μM.

Zinc (e.g. $ZnCl_2$) may be added with (e.g. concurrently with) the reprogramming transcription factors (e.g. PAX4). In preferred embodiments, zinc is added with PDX1, MAFA, NGN3 and PAX4.

Zinc (e.g. $ZnCl_2$) may be added with inhibition of ARX. In some embodiments, treatment with reprogramming transcription factors, inhibition of ARX and treatment with zinc are all concurrent.

In another aspect the invention relates to the use of zinc to enhance reprogramming of pancreatic cells to beta-like cells, where the reprogramming is carried out using factors and conditions as described herein.

Other Cells

Methods described herein may be used to obtain alpha-like cells. In these methods preferred combinations of transcription factors for treating pancreatic cells include combinations comprising, consisting or consisting essentially of:

MAFA and NGN3;
PDX1, MAFA and PAX4;
PDX1, MAFA and NGN3;
PDX1, MAFA, NGN3 and PAX4 (condition 29);
PDX1, MAFA, PAX4 and NKX6.1 (condition 28);
PDX1, PAX4, NGN3 and NKX6.1 (condition 23);
MAFA, PAX4, NGN3 and NKX6.1 (condition 19);
MAFA, PAX4, NGN3 and NKX6.1, ND1 (condition 9);
or
MAFA (condition 4).

Preferred combinations of transcription factors for use in methods to obtain alpha-cells include combinations consisting of:
PDX1, MAFA, PAX4 and NKX6.1 (condition 28);
PDX1, PAX4, NGN3 and NKX6.1 (condition 23);
MAFA, PAX4, NGN3 and NKX6.1 (condition 19); or
MAFA, PAX4, NGN3, NKX6.1 and ND1 (condition 9).

Particularly preferred combinations comprise, consist or consist essentially of:
PDX1, MAFA, PAX4 and NKX6.1 (condition 28);
PDX1, PAX4, NGN3 and NKX6.1 (condition 23);
MAFA, PAX4, NGN3 and NKX6.1 (condition 19).

Most preferred is a combination comprising, consisting or consisting essentially of: MAFA, PAX4, NGN3 and NKX6.1 (condition 19).

In preferred methods for obtaining alpha-like cells, the transcription factor(s) include NKX6.1.

Methods described herein may be used to obtain delta-like cells. In these methods preferred combinations of transcription factors for treating pancreatic cells include combinations comprising, consisting or consisting essentially of:
PDX1, MAFA, PAX4 and ND1 (condition 27);
PDX1, MAFA, NGN3 and ND1 (condition 25);
MAFA, PAX4, NGN3 and NKX6.1, ND1 (condition 9); or
MAFA (condition 4).

In preferred methods for obtaining delta-like cells, the transcription factor(s) include NeuroD1.

Alternative combinations of reprogramming transcription factors that may be used for obtaining endocrine cells include those shown in FIG. 1C. Accordingly, methods of the present invention may comprise treating the cells with combination of transcription factors that comprise, consist or consist essentially of the combinations shown in FIG. 1C.

Culture

In addition to the above factors, soluble factors (SFs) may be used, including betacellulin, exendin-4 and nicotinamide, EMT inhibitors and chromatin modifying agents as described herein.

The methods of the invention may involve culturing the cells in the presence of one or more of betacellulin, exendin-4 and nicotinamide. In some embodiments the method involves culturing the cells in the presence of all of betacellulin, exendin-4 and nicotinamide (BEN). In some embodiments treatment with one or more of betacellulin, exendin-4 and nicotinamide follows culture with the transcription factor(s). In some embodiments there is overlap between culture with one or more of betacellulin, exendin-4 and nicotinamide and the transcription factor(s). In some embodiments the cells are cultured simultaneously with transcription factors and one or more of betacellulin, exendin-4 and nicotinamide.

In some embodiments the cells are cultured in the presence of one or more of betacellulin, exendin-4 and nicotinamide for 3-10 days, for example, 4-7 days, preferably about 6 days. Betacellulin, exendin-4 and/or nicotinamide may be added for example 0-3, e.g. about 1, 2 or 3 days after treatment with the transcription factors begins. Preferably the cells are cultured in the presence of betacellulin, exendin-4 and/or nicotinamide for a time frame overlapping with treatment with the transcription factor(s). By way of non-limiting examiner, the cells may be cultured for 6 days with BEN overlapping with treatment with the transcription factor(s).

Media supplemented with betacellulin, exendin-4 and/or nicotinamide may be added to the cells treated with the transcription factor(s). In some embodiments the media is changed about every 1, 2 or 3 days but it can be changed more or less frequently than this.

The cells may be pre-treated to inhibit dedifferentiation of epithelial cells to mesenchymal cells (the epithelial-mesenchymal transition (EMT)). Accordingly, in some embodiments, cells are treated with inhibitors of EMT, for example, inhibitors of the Rho-associated protein kinase (Rock) signalling pathway and/or transforming growth factor beta 1 (TGFbeta1) signalling pathway. In some embodiments the inhibitors are small molecule inhibitors.

In this context, inhibitors of EMT may be referred to as inhibitors of dedifferentiation and are factors that suppress EMT or dedifferentiation.

Exemplary Rock pathway inhibitors include Y27632 (Y2) (chemical name: (R)-(+)-trans-4-(1-Aminoethyl)-N-(4-Pyridyl)cyclohexanecarboxamide dihydrochloride; Uehata, M et al. (1997) *Nature* 389 (6654): 990-4). Y2 is obtainable, for example, from Sigma-Aldrich Catalogue No. Y0503.

Exemplary TGFbeta1 pathway inhibitors include SB43152 (SB) (chemical name: 4-(5-Benzol[1,3]dioxol-5-yl-4-pyridin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate; Laping et al. (2002). Molecular Pharmacology 62 (1): 58-64.) SB is obtainable, for example, from Sigma-Aldrich Catalogue No. S4317.

An alternative TGFbeta1 pathway inhibitor is SB505124 (obtainable from Sigma-Aldrich; Catalogue No. S4696)

The cells may also be pre-treated with one or more chromatin modifying agents, for example a DNA-methyltransferase inhibitor and/or a histone deacetylase (HDAC) inhibitor. Exemplary DNA-methyltransferase inhibitors include 5-Aza-2'deoxycytidine (aza). Exemplary HDAC inhibitors include sodium butyrate (NaBu). In a preferred embodiment, the cells are pretreated with a DNA-methyltransferase inhibitor and/or a histone deacetylase (HDAC) inhibitor.

In some embodiments the cells are cultured/pre-treated with the inhibitors of epithelial-mesenchymal transitions and the chromatin modifying agents simultaneously.

The pre-treatment is carried out prior to treating the cells with one or more transcription factors. Pre-treatment may be carried out for 1-5 days, for example, 2-4 days, preferably for 3 days.

At the end of the pre-treatment period, the cells may be washed before treatment with the transcription factors.

Implementation of the Edmonton protocol facilitated access to human cadaveric tissue that results as a by-product of the islet isolation procedure. When placed in culture, this exocrine enriched fraction rapidly dedifferentiates to form a mesenchymal monolayer that can be expanded through 20 or more passages (Montgomery and Yebra, 2011).

Several studies have attempted to expand β-cell numbers through redifferentiation of these human exocrine or islet derived mesenchymal cells (Bar et al., 2012; Davani et al., 2007; Gershengorn et al., 2004; Hao et al., 2006; Ouziel-Yahalom et al., 2006). Despite some success in generating glucose-responsive insulin producing cells from both islet and exocrine cell sources, the ability of the transdifferentiated cells to rescue diabetes in an animal model is still unclear.

In the methods of the present invention the cells may be reprogrammed to endocrine cells directly from exocrine cells without fully entering a mesenchymal state. As explained above, the methods of the present invention may comprise culturing the cells to allow an initial stage of epithelial-to-mesenchymal transition (EMT), followed by inhibition of EMT before completion of EMT.

Therefore, the methods of the present invention may include a step of culturing the cells in adherent culture to allow attachment prior to treatment with transcription factors. The cells may be cultured in adherent culture for half a day up to 7 days prior to treatment with transcription factors.

In preferred embodiments, the pancreatic cells may be cultured for half a day to 3 days prior to pre-treatment with an inhibitor of epithelial to mesenchymal transition (e.g. a Rock signalling pathway inhibitor and/or a TGFbeta1 signalling pathway inhibitor) as described herein. Preferably the cells maybe cultured for 1-2 days, for example, for about 2 days before pre-treatment.

Therefore, in some preferred methods of the invention, the methods comprise, consist or consist essentially of:
a) culturing pancreatic cells in adherent culture; then
b) reprogramming the cells, comprising:
  (i) pre-treating the cells inhibitors of epithelial to mesenchymal transition, then
  (ii) treating the cells with one or more transcription factors; and optionally
  (iii) treating the cells with betacellulin, exendin-4 and nicotinamide.

Preferably, the cells are cultured in a monolayer. Preferred culture times and conditions, such as glucose concentration and presence of laminin, are detailed elsewhere herein.

In the methods of the present invention, the cells may be cultured in serum-free or serum-containing medium. Preferably, the cells are cultured in serum-free medium (SFM). The cells may be cultured in SFM throughout the method. The cells may be cultured in SFM throughout the reprogramming, i.e. from the pre-treatment step onwards. The culture medium may be changed every 1-3 days, for example about every 1, 2 or 3 days.

Figure 4:
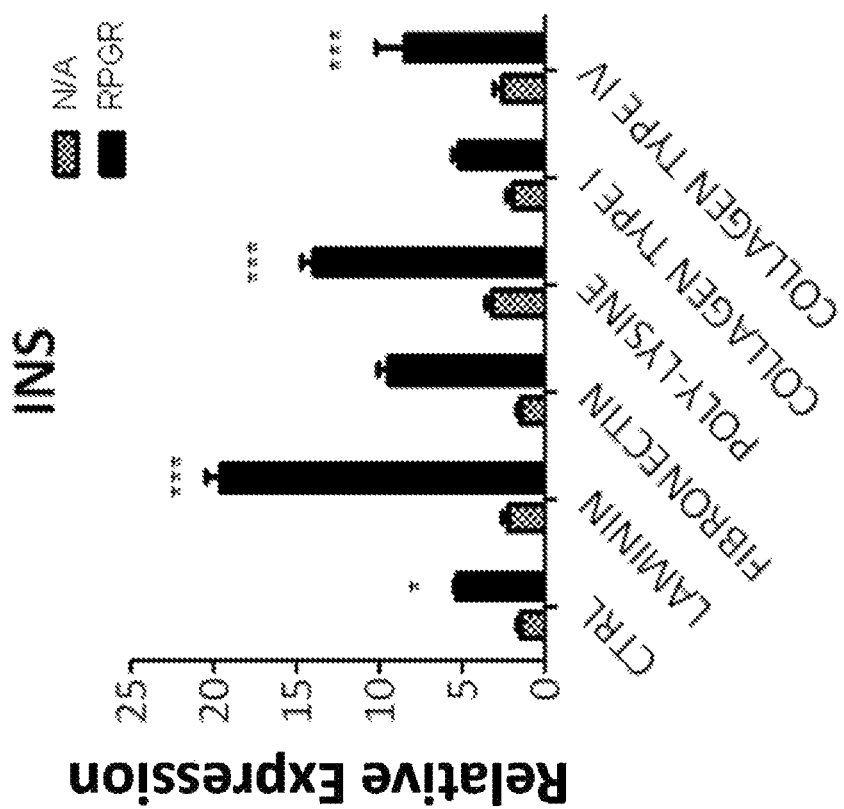

The present inventors have shown that the culturing the cells on laminin improves the efficiency of reprogramming of the cells (see Examples and FIG. 4). Therefore, in a preferred embodiment of the present invention, the cells are cultured on laminin, for example on laminin coated plates. The cells may be cultured on laminin during the reprogramming step, or preferably throughout the method.

The laminin used in the methods may comprise multiple isoforms. For example, the laminin may comprise the isoform LAM-111. In some embodiments LAM-111 is the most abundant isoform of laminin used in the methods. The laminin may be obtained from Engelbreth-Holm-Swarm (EHS) mouse sarcoma, for example.

In one aspect the invention provides use of laminin to enhance reprogramming of pancreatic cells (e.g. exocrine cells) toward endocrine cells (e.g. beta-like cells). Use of a laminin may be in conjunction with the conditions, including factors and agents that are used in the methods of reprogramming described herein.

Recent studies in mice have shown that glucose metabolism is a key regulator of compensatory β-cell proliferation (Porat et al., 2011). Porat et al. propose a mechanism for homeostasis of beta-cell proliferation and mass involving adjustment of proliferation according to the rate of glycolysis.

Figure 5:
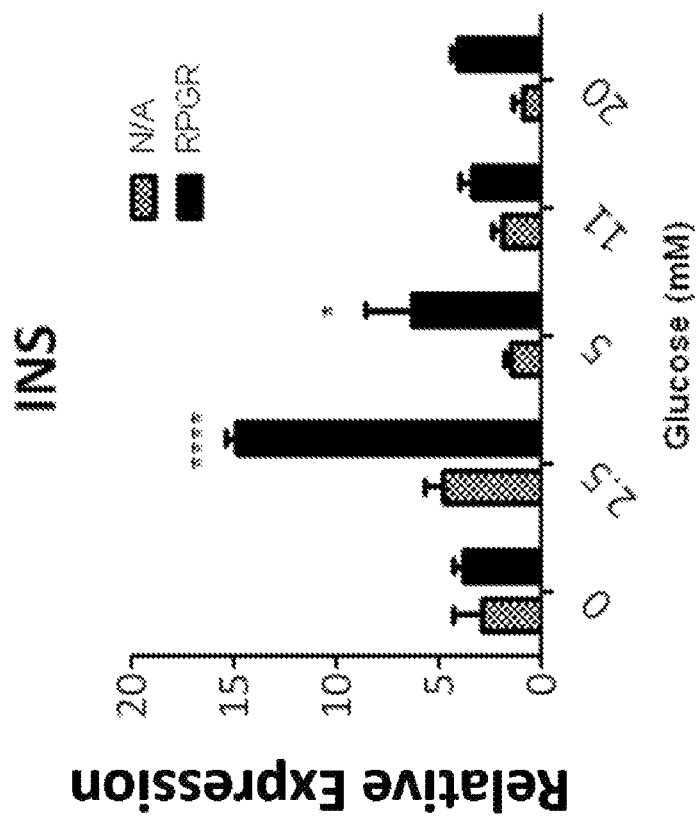

The present inventors have shown that culturing the cells in low glucose further enhances reprogramming towards beta-cells (see Examples and FIG. 5). Therefore, in one embodiment of the invention the cells are cultured in low glucose concentrations. The cells may be cultured in low glucose concentrations during the reprogramming step or throughout the method. Preferably, the cells are cultured in low glucose concentrations throughout the reprogramming step. For example, the cells may be cultured in low glucose concentrations for about 5-15 days or 7-12 days, for example for about 10 days. Glucose may be added to the medium (e.g. SFM) that is used in the reprogramming step. The glucose concentration level may be between 0-5 mM, for example between 0.5-4.5 mM, 1-5 mM, 1-4.5 mM, 1-4 mM, 1.5-4.5 mM, 1.5-4 mM. In particular the glucose concentration may be between 2-4.5 mM, 2-4 mM, 2-3 mM. In one embodiment the cells are cultured in a concentration of about 2.5 mM glucose.

In one aspect the invention provides use of low glucose culture (e.g. concentrations of 5 mM or less) to enhance reprogramming of pancreatic cells (e.g. exocrine cells) toward endocrine cells (e.g. beta-like cells). Use of the low glucose concentration culture may be in conjunction with the conditions, including factors and agents that are used in the methods of reprogramming described herein.

Clinical and Other Uses

The endocrine cells (for example including beta-like cells) obtained by methods of the present invention may be used to produce insulin, preferably in vivo or ex vivo.

The endocrine cells (for example including alpha-like cells) obtained by methods of the present invention may be used to produce glucagon, preferably in vivo or ex vivo.

The endocrine cells (for example including delta-like cells) obtained by methods of the present invention may be used to produce somatostatin, preferably in vivo or ex vivo.

The endocrine cells (for example including beta-like cells) obtained by methods of the present invention have particular utility in clinical situations to treat diabetes.

The cell population obtained by the methods may be used directly, or optionally may be subject to further steps, for example to prepare the cells population for clinical use, or to enrich it for certain cells (e.g. cells capable of producing insulin). Furthermore sub-sets of epithelial cells may be isolated from the population for use as required.

Therefore, the present invention includes endocrine cells (especially beta-like cells) obtained by the methods described herein for use in a method of treatment by therapy, for example for treating diabetes in a patient.

The term "treatment," as used herein in the context of treating a condition, pertains generally to treatment and therapy of a human, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. "Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

Patients to be treated include those suffering from (diagnosed with) diabetes.

Treatment of diabetes in the context of the present invention may be treatment of type-1 diabetes or other causes leading to insulin deficiency e.g. post-pancreatectomy. The treatment may also be of type-2 diabetes.

In some embodiments the patients to be treated may be C-peptide negative.

Additionally or alternatively, the patient may display, or have displayed, severe episodes of hypoglycaemia and/or reduced ability to detect the symptoms of impending hypoglycaemia.

The cells can be delivered in a therapeutically-effective amount.

The term "therapeutically-effective amount" as used herein, pertains to that amount of the receptor or ligand which is effective for producing some desired therapeutic effect, such as restoration of hypoglycaemic awareness, or independent of the need for external insulin, commensurate with a reasonable benefit/risk ratio, when administered in accordance with a desired treatment regimen.

Thus the invention also relates to methods of treatment of diabetes using beta-like cells obtained by the methods described herein.

The invention also relates to use of islet cells obtained by the methods described herein for use in the preparation of a medicament for treatment of diabetes.

Beta-like cells obtained by the methods described herein may be administered to a patient, for example they may be used in cell or cellular therapy. The beta-like cells obtained by the methods described herein may be transplanted into patients. Such cells may be manipulated before use e.g. encapsulated. The cells may be utilised in an external or implantable device or container.

Preferably the treatment is based on the Edmonton Protocol and may comprise the steps of infusing the islet into the patient, for example the patient's portal vein, optionally in conjunction with one or more (e.g. two) immunosuppressants (for example sirolimus and tacrolimus) and\or a monoclonal antibody intended to prevent organ rejection (for example daclizumab). The particular protocol would be at the discretion of the physician who would also select dosages using his/her common general knowledge and dosing regimens known to a skilled practitioner.

Variant Sequences

It will be appreciated that reference herein to transcription factors (including PDX1, MAFA, PAX4, NGN3, NKX6.1 and ND1) and other factors (e.g. betacellulin, exendin-4 and nicotinamide) includes those embodiments described above, as well as sequence variants or fragments (e.g. protein fragments of at least 25, 50, 100, 150, 200, 250, 300, 350, 400, 450 or more amino acids in length) which retain the ability to direct the specific function of the factor, including for example reprogramming to endocrine-type cells.

For example, non-human variants may be used. Examples include variants of primate, rodent, porcine, bovine, canine, equine, feline origin.

Any such variants or fragments may be used in the methods of the present invention, for example, either in methods involving contacting the cells protein preparations of the transcription factors, or methods involving expressing the transcription factors in the cells.

Polypeptides or peptides that have substantial identity to the representative amino acid sequences provided herein for the transcription factors may also be used. Similarly, nucleotide sequences encoding any of these polypeptides, peptides or proteins, or nucleotide sequences having substantial identity thereto, may be used in the methods of the present invention.

Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, or 99% identity over a specified region. The term "identity" refers to sequence similarity between two polypeptides molecules. Identity can be determined by comparing each position in the aligned sequences.

A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.genome.ad.ip, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85:2444, and the computerised implementations of these algorithms (such as GAP, BEST-FIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). For example, the "BLAST 2 Sequences" tool, available through the National Center for Biotechnology Information (through the internet at http://www.ncbi.nlm.nih.gov/BLAST/b12seq/wblast2.cqi) may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by visual inspection.

Methods and Materials for Target Inhibition

Inhibition of ARX expression in the context of the present invention may use small inhibitory RNAs (siRNAs). ARX gene expression can be reduced by contacting the cell with a small double stranded RNA (dsRNA), or a vector or construct causing the production of a small double stranded RNA, such that ARX gene expression is specifically inhibited (i.e. RNA interference or RNAi). Methods for selecting an appropriate dsRNA or dsRNA-encoding vector are well known in the art for genes whose sequence is known (e.g. U.S. Pat. Nos. 6,573,099 and 6,506,559; and International Patent Publication Nos. WO 01/36646, WO 99/32619, and WO 01/68836). Antisense oligonucleotide constructs can also function as inhibitors of ARX gene expression for use in the present invention. Anti-sense oligonucleotides, including anti-sense RNA molecules and anti-sense DNA molecules, would act to directly block the translation of ARX mRNA by binding thereto and thus preventing protein translation or increasing mRNA degradation, thus decreasing the level of ARX protein, and thus activity, in a cell. For example, antisense oligonucleotides of at least 10 consecutive bases from the sequence, more preferably at least 15 (e.g. at least 20, 25) bases and complementary to unique regions of the mRNA transcript sequence encoding ARX can be synthesized and administered, e.g., by conventional phosphodiester techniques. Perfect complementarily between the sequence of the antisense molecule and that of the target gene or messenger RNA is not required, but is generally preferred. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Ribozymes can also function as inhibitors of ARX gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of ARX mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays. Both antisense oligonucleotides, siRNAs and ribozymes useful as inhibitors of ARX gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Expression Vectors

Where the methods involve expressing the transcription factors (e.g. PAX4) in the cell, this may involve transfecting or transducing the cell with nucleic acids encoding the differentiation factors.

Generally speaking, those skilled in the art are well able to construct vectors and design protocols for recombinant gene expression. Suitable vectors can be chosen or constructed, containing, in addition to the elements of the invention described above, appropriate regulatory sequences, including promoter sequences, terminator fragments, polyadenylation sequences, marker genes and other sequences as appropriate. For further details see, for example, Molecular Cloning: a Laboratory Manual: 2nd edition, Sambrook et al, 1989, Cold Spring Harbor Laboratory Press or Current Protocols in Molecular Biology, Second Edition, Ausubel et al. eds., John Wley & Sons, (1995, and periodic supplements).

Expression of the factors may involve expression from an expression vector, in particular a mammalian expression vector. The expression vector may be of any suitable structure which provides expression of the factors. As will be appreciated, a suitable promoter will be operably linked to the coding region for the particular factor. For example, a coding sequence is operably linked to a promoter if the promoter activates the transcription of the coding sequence. Preferably the transcription factors comprise PAX4.

Suitable expression systems are well known in the art and do not per se form part of the present invention. Particular example nucleic acid delivery systems are summarised in WO2012/006440.

Vectors include but are not limited to, plasmids, cosmids, DNA or RNA viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors. Preferred viruses which can be used to generate viral vectors are retroviruses (Miller et al., Am. J. Clin. Oncol., 15(3): 216-221, 1992) and lentiviruses. Lentiviral vectors are well known in the art (see, for example, Naldini et ah, Science, 272(5259):263-267, 1996; Zufierey et al., Nat. Biotechnol., 15(9):871-875, 1997; Blomer et al., J. Virol, 71(9): 6641-6649, 1997; U.S. Pat. Nos. 6,013,516 and 5,994,136). Lentiviral vectors are a special type of retroviral vector which are typically characterized by having a long incubation period for infection. Furthermore, lentiviral vectors can infect non-dividing cells. Lentiviral vectors are based on the nucleic acid backbone of a virus from the lentiviral family of viruses. Typically, a lentiviral vector contains the 5' and 3' LTR regions of a lentivirus, such as SIV and HIV. Lentiviral vectors also typically contain the Rev Responsive Element (RRE) of a lentivirus, such as SIV and HIV. Examples of lentiviral vectors include those of Dull, T. et al., "A Third-generation lentivirus vector with a conditional packaging system" J. Virol 72(11):8463-71 (1998);

For example, an adenovirus vector may be used to carry cDNA of human transcription factors (e.g. including PAX4).

Aspects of the invention described herein may be used with the conditions, cells, factors and methods described in GB Patent Application (GB1408570.8). The content of GB1408570.8 is incorporated herein by cross-reference. In particular the examples and experimental data shown in GB1408570.8 are incorporated herein by reference.

Aspects of the invention described herein may be used with the conditions, cells, factors and methods described in GB Patent Application that was filed on the same day as the present application. The content of GB Patent Application is incorporated herein by cross-reference. In particular the examples and experimental data shown in GB Patent Application are incorporated herein by reference.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1. Combinations of transcription factors (TFs) induce reprogramming of human exocrine enriched fraction (EEF). (A) EEF cells were cultured as a monolayer for two days and then treated with SB, Y2, Aza and NaBu for 3 days. The cells were then transduced with various combinations of adenoviruses containing TFs (AD-TFs) as indicated and further cultured in presence of BEN for 6 days. (B) Insulin mRNA levels were measured by RT/QPCR. (C) Layout of the different transcription factor combinations used during the transdifferentiation process. Combinations of TFs that generated highest levels of insulin mRNA were indicated in yellow. N/A refers to untreated EEFs and SF to soluble factors in absence of Ad-TFs.

Figure 2:
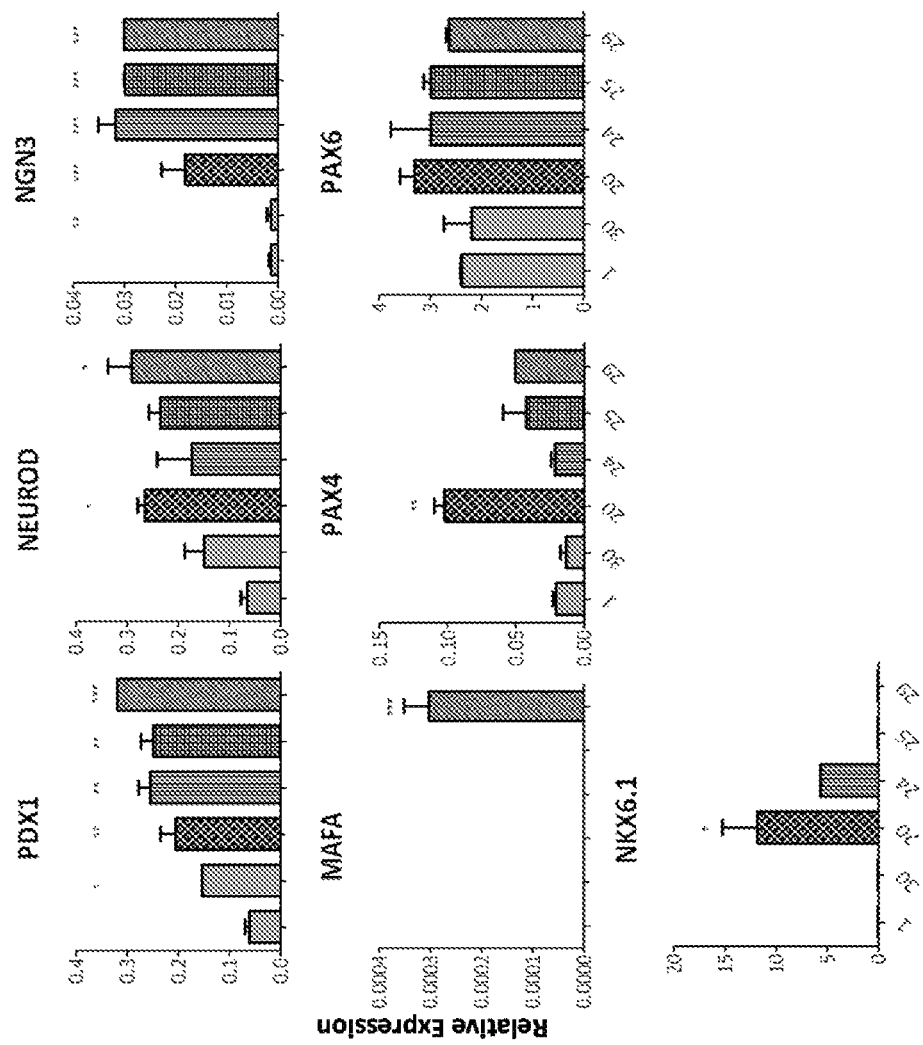

FIG. 2. Four combinations of TFs induce expression of insulin (FIG. 1) and endogenous pancreatic TFs PDX1, NeuroD1, NGN3, MAFA, PAX4, PAX6 and NKX6.1 suggesting that the exogenous TFs are inducing reprogramming or transdifferentiation of the EEFs towards β-cells. Condition 1 is untreated cells, conditions 30 is cells treated with soluble factors in absence of Ad-TFs. Condition 20, PDX1/NGN3/NKX6.1/NeuroD1; condition 24, PDX1/MAFA/NKX6.1/NeuroD1; condition 25, PDX1/MAFA/NGN3/NeuroD1; and condition 29, PDX1/MAFA/NGN3/PAX4. SFs are BEN, Y2, SB, 5-Aza-2'deoxycytidine (Az) and sodium butyrate (NaBu).

Figure 3:

FIG. 3. Condition 29 is the only combination of TFs to provide glucose stimulated insulin (C-peptide) secretion. These data suggest that the presence of exogenous PAX4 is essential for efficient reprogramming of EEFs towards functional glucose sensitive β-cells.

FIG. 4. Culture on laminin promotes the reprogramming of EEFs towards insulin-expressing β-cells by combinations of PDX1/NGN3/MAFA and PAX4.

FIG. 5. Culture in low glucose promotes efficient reprogramming of EEFs towards insulin-expressing β-like cells.

Figure 6:
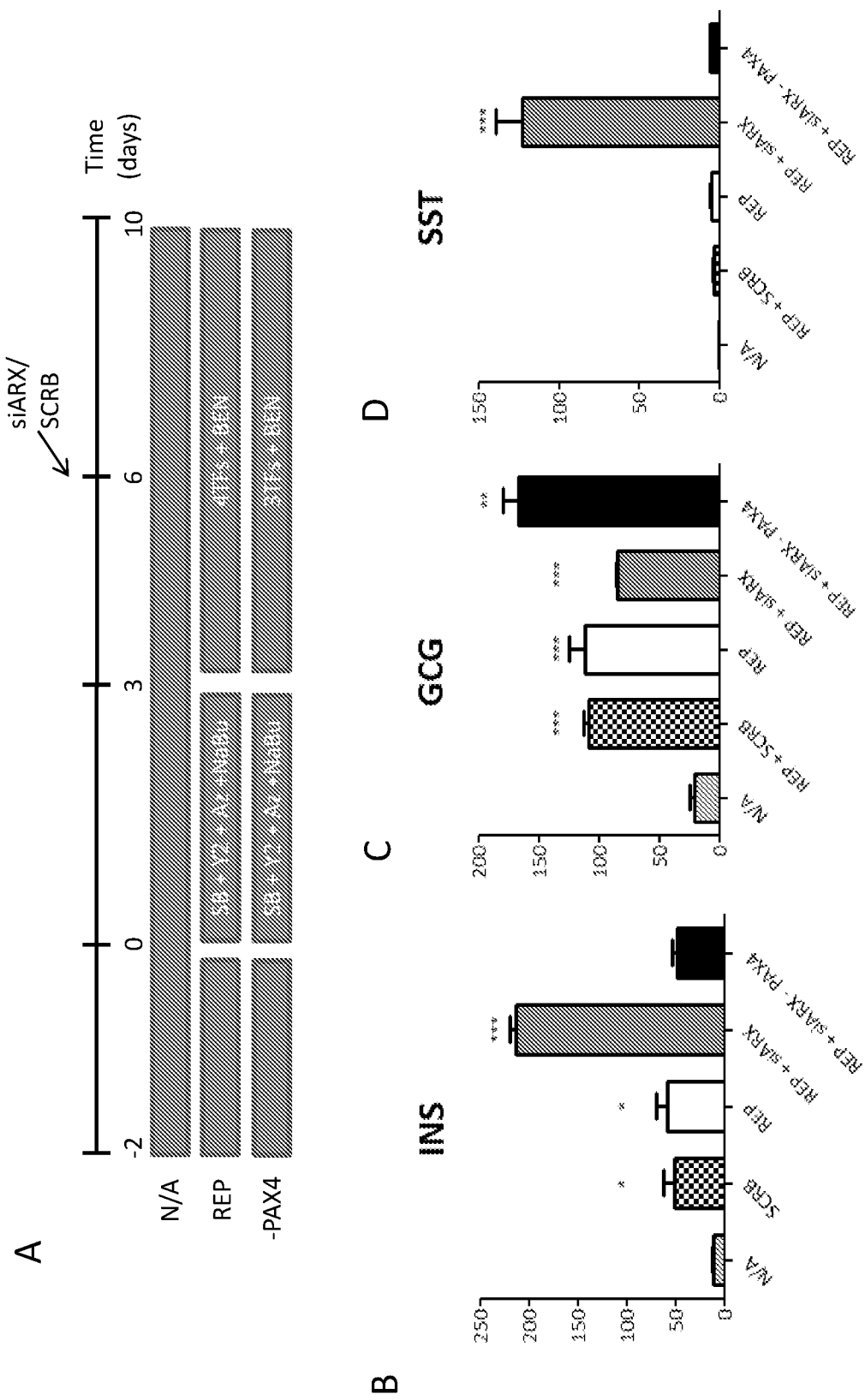

FIG. 6. Knock-down of the endogenous TF ARX by siRNA on day 6 promotes efficient reprogramming of EEFs (FIG. 6B). Experimental protocol is illustrated in FIG. 6A. N/A refers to untreated EEFs and SF to soluble factors in absence of Ad-TFs. SCRB refers to a non-specific, non targeting siRNA. (B) insulin expression (C) glucagon expression; (D) somatostatin expression.

Figure 7:
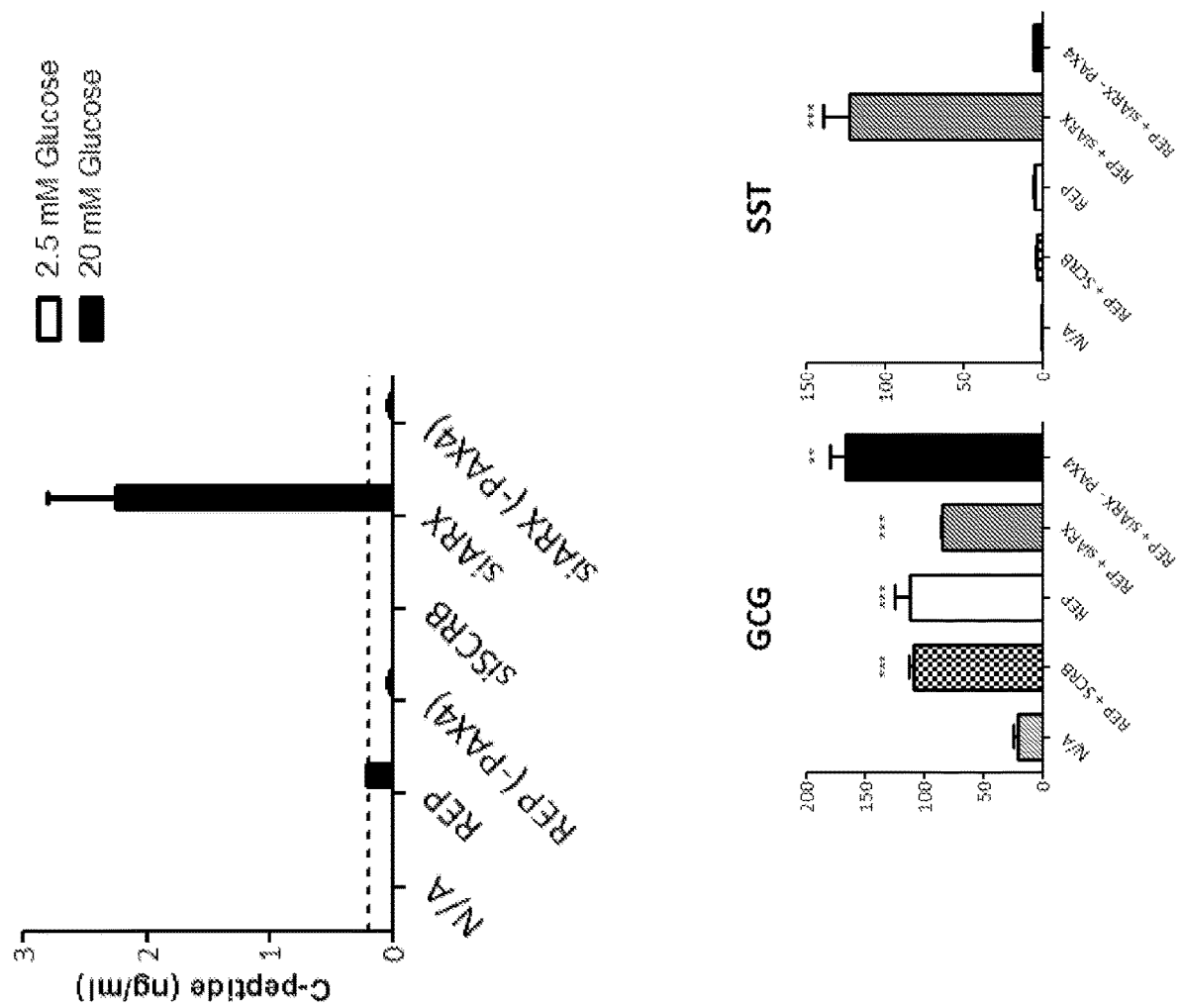

FIG. 7. Knock-down of the endogenous TF ARX increases glucose-sensitive insulin (C-peptide) secretion in reprogrammed exocrine tissue. This effect is dependent on exogenous PAX4.

Figure 8:
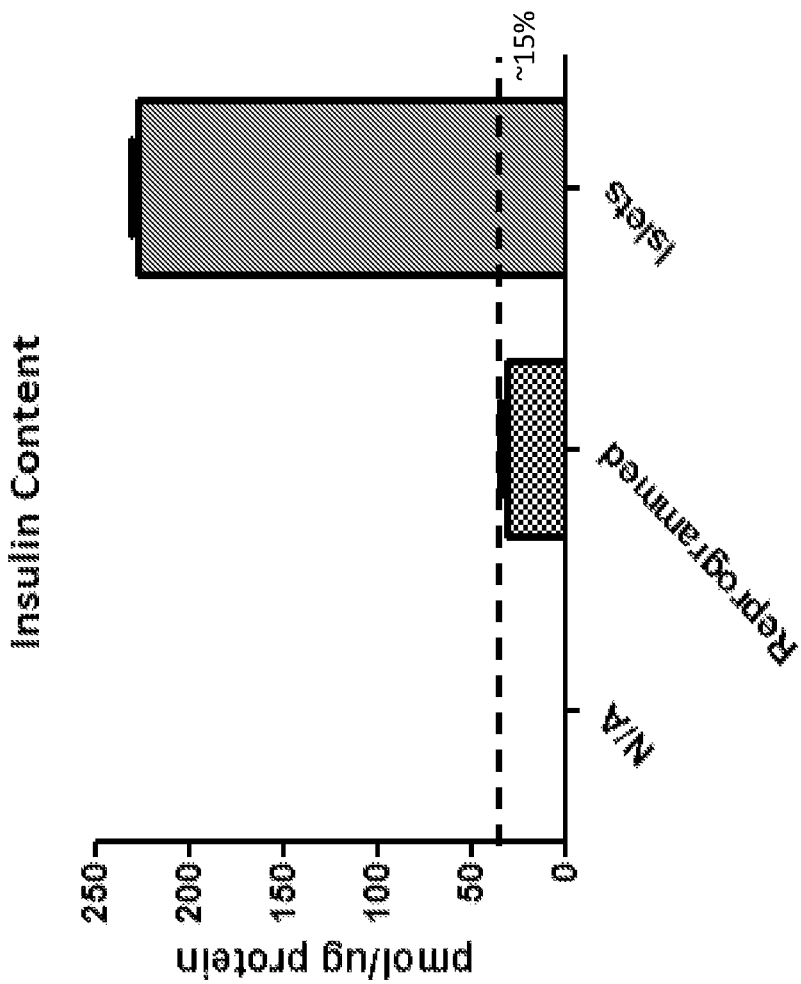

FIG. 8. Reprogrammed islets express insulin at levels around 15% of that in adult human islets. To reprogram EEF cells were cultured as a monolayer for two days and then treated with SB, Y2, Aza and NaBu for 3 days. The cells were transduced with PDX1/MAFA/NGN3/PAX4 and cultured in presence of BEN for 6 days. Silencing of endogenous transcription factor (TF) ARX by siRNA was carried out at day 6 post addition of SB, Y2, Aza and NaBu.

Figure 9:
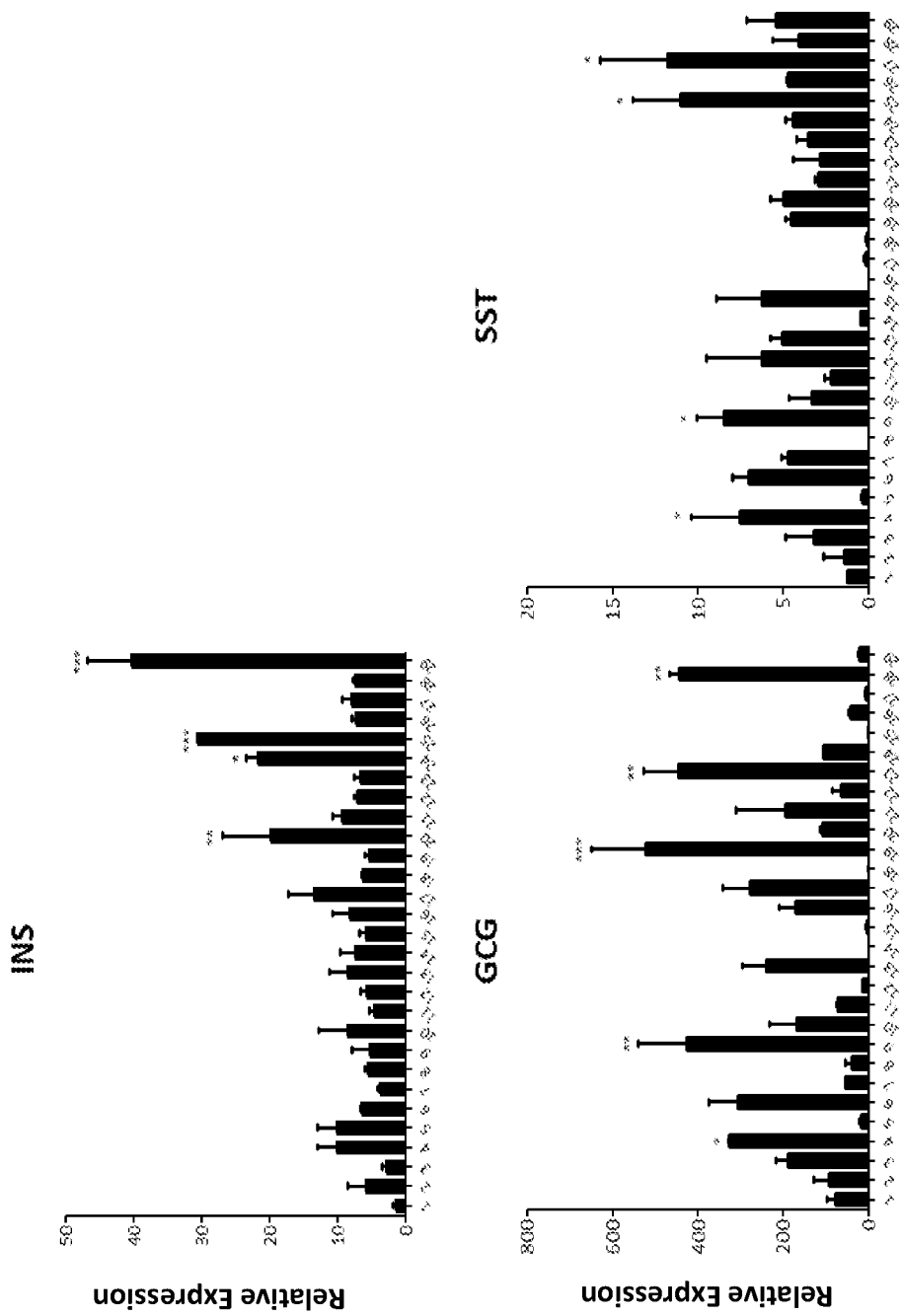

FIG. 9. Role of endocrine transcription factors on transdifferentiation. RT-qPCR analysis of the endocrine hormones insulin, glucagon and somatostatin after treatment with each transcription factor combination. Layout of the different transcription factor combinations used during the transdifferentiation process is shown in FIG. 1C. Data are representative of triplicate experiments and are relative to glyceraldehyde 3-phosphate dehydrogenase.

Figure 10:
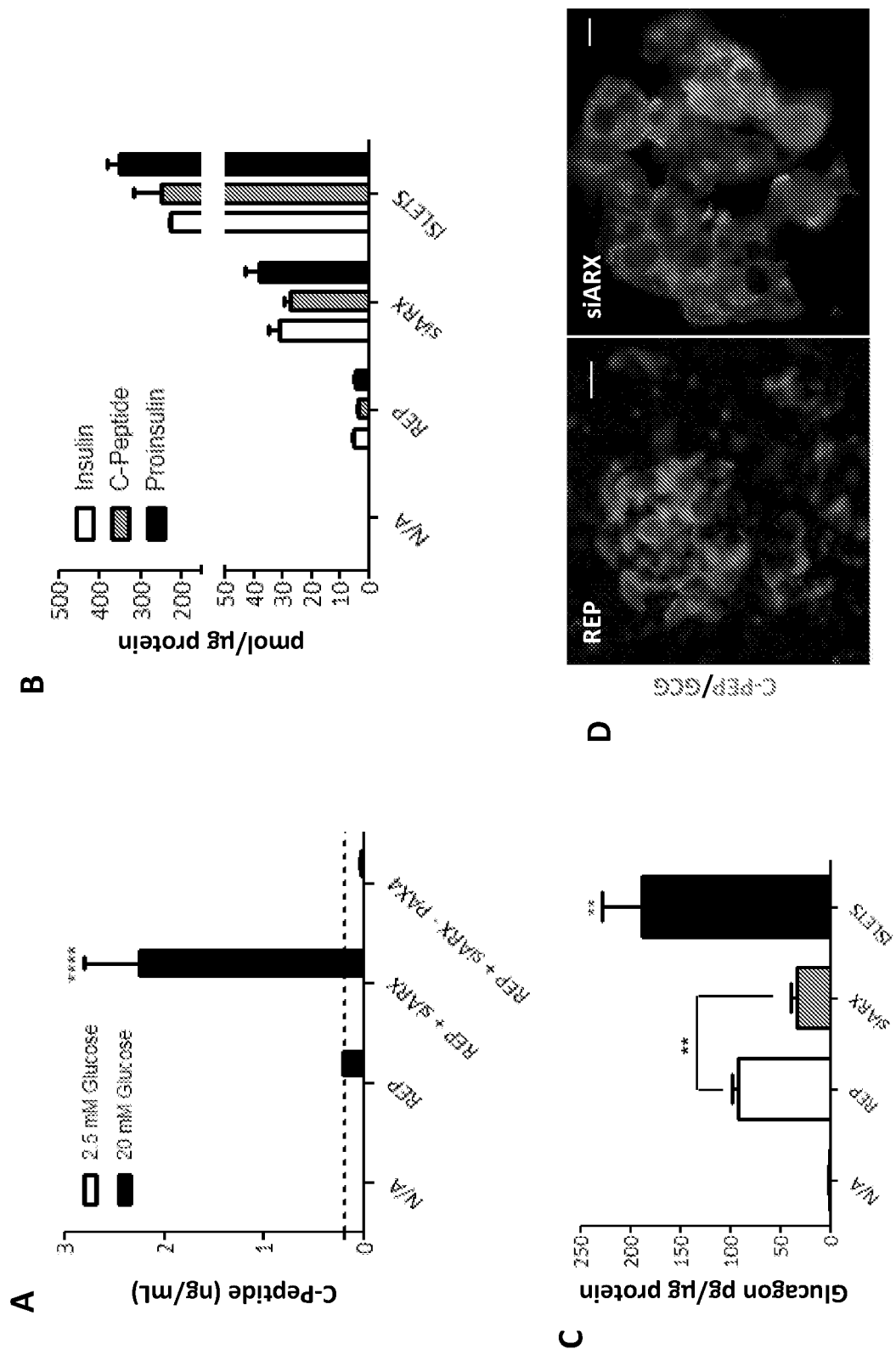

FIG. 10. ARX inhibition enhances beta cell maturation and decreases alpha cell differentiation. (A) C-peptide release by untreated (N/A), transdifferentiated cells in the absence of siARX (REP), siARX transdifferentiated cells (siARX) and in the absence of PAX4 (siARX-PAX4). C-peptide was detected from the culture medium by a specific human C-peptide ELISA. Data are representative of triplicate experiments. (B) Insulin, C-peptide and Proinsulin content of untreated, transdifferentiated cells in the absence of siARX (REP), siARX transdifferentiated cells (siARX) and human islets. The content of each peptide was detected by specific human ELISAs after cell lysis and normalised to the total protein content. Data are representative of triplicate experiments. (C) Glucagon content of untreated, transdifferentiated cells in the absence of siARX (REP), siARX transdifferentiated cells (siARX) and human islets. Glucagon was detected by a specific human ELISA after cell lysis and normalised to the total protein content. Data are representative of triplicate experiments. (D) Immunocytochemistry for glucagon and C-peptide in transdifferentiated cells in the absence of siARX (REP) and siARX transdifferentiated cells (siARX). Data are representative of triplicate experiments. Scale bar=20 µm.

Figure 11:
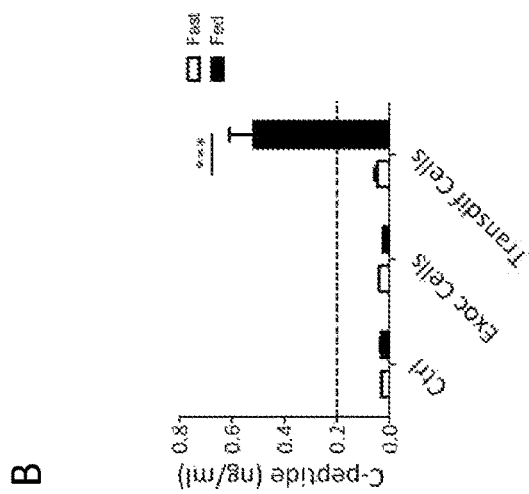
Figure 11:
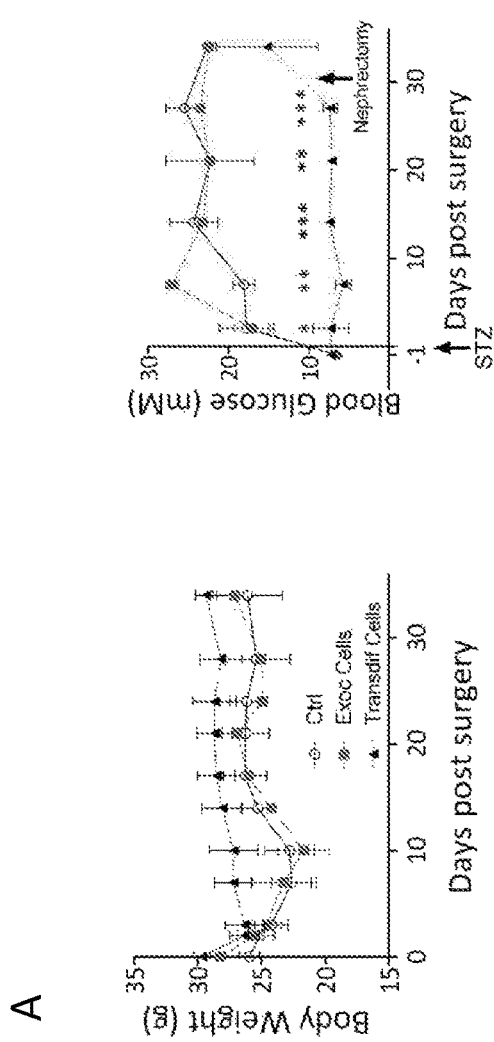
Figure 11:
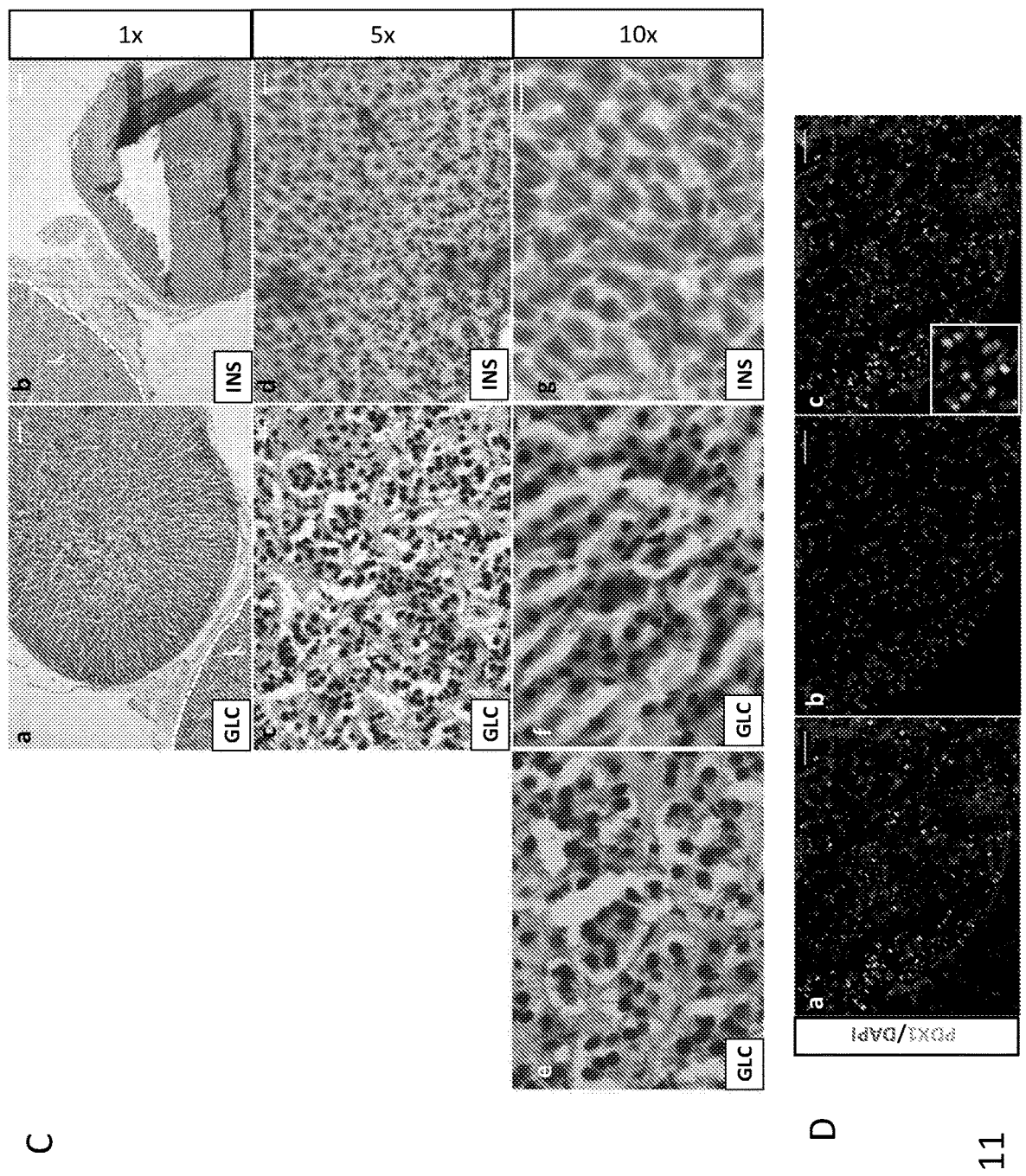

FIG. 11. Reprogrammed insulin producing cells prevent STZ-induced diabetes in vivo. (A) Body weight and blood glucose levels were measured in NOD/SCID mice grafted with transdifferentiated cells (Transdif Cells), exocrine pancreatic cells (Exoc Cells) or in non grafted mice (Ctrl) over a 38 day period after surgery. A single dose (150 mg/kg) streptozotocin was administered one day prior to surgery. n=5 Transdiff cells; n=3 Exoc cells; n=2 Ctrl. (B) Serum C-peptide levels were measured in NOD/SCID mice grafted with transdifferentiated cells (Transdif Cells) or exocrine pancreatic cells (Exoc Cells) and in non grafted mice (Ctrl) after a 4 h starvation period (fast) or under ad libitum feeding (fed) conditions. n=5 Transdiff cells; n=3 Exoc cells; n=2 Ctrl. (C) Immunostaining for insulin and glucagon of grafted kidneys following kidney removal. Yellow dash lines indicate the border between the kidney (k) and the graft. The red circle in panel a indicates the difference in glucagon staining observed within the cluster. A 5× higher magnification of the cells inside this circle is shown in panel c. 10× higher magnifications of the cells inside (e) and outside (f) the circle is shown. Panel d shows a 5× higher magnification of insulin staining within the area marked by the red square in panel b. A 10× higher magnification of insulin positive cells present in the centre of the cluster is shown in panel g. Scale bar for a and b=100 µm. Scale bar for c-g=20 µm. (D) Immunofluorescent staining for PDX1 in kidneys grafted with transdifferentiated cells. Scale bar=50 µm. A 5× higher magnification inlet is shown.

Figure 12:
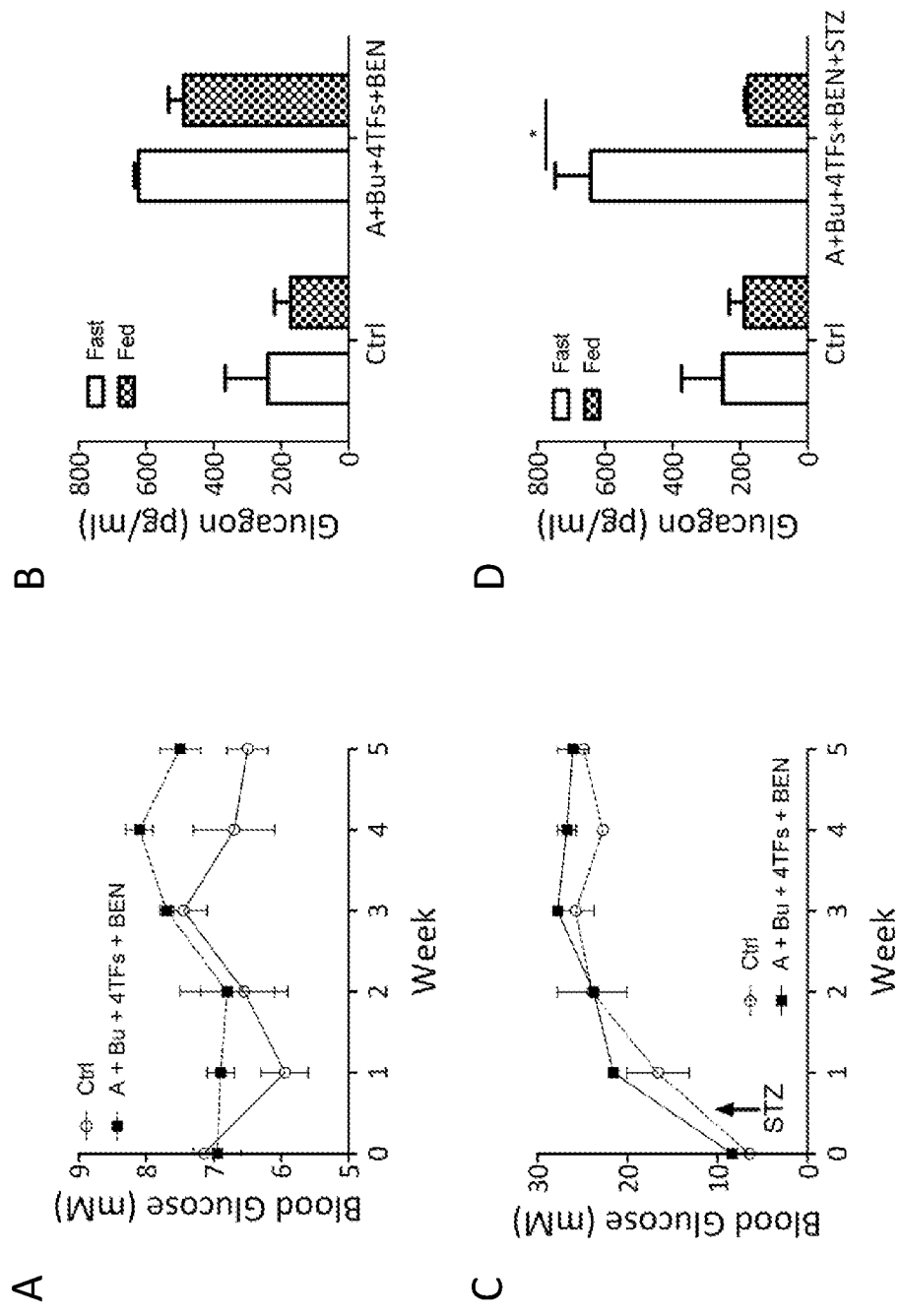

FIG. 12. Transdifferentiated pancreatic mesenchymal stem cells (MSCs) release glucagon in a regulated manner in vivo. (A) Blood glucose levels were measured in NOD/SCID mice grafted (A+Bu+4TFs+BEN) and in non grafted mice (Ctrl) over an 18 week period. n=5 animals in each group. (B) Glucagon was measured from the serum of grafted animals after a 4 h starvation period (fast) or under ad libitum feeding (fed) conditions. n=5 animals in each group. (C) NOD/SCID mice were rendered diabetic with one dose (150 mg/kg) of streptozotocin, one day prior to surgery. Blood glucose levels were measured in grafted (A+Bu+4TFs+BEN) and in non grafted mice (Ctrl) over an 18 week period. n=5 animals in each group. (D) NOD/SCID mice were rendered diabetic with one dose (150 mg/kg) of streptozotocin, one day prior to surgery (D) Glucagon was measured from the serum of grafted animals after a 4 h starvation period (fast) or under ad libitum feeding (fed) conditions. n=5 animals in each group. A, 5-Aza-2'deoxycytidine (aza); Bu sodium butyrate (NaBu).

Figure 13:
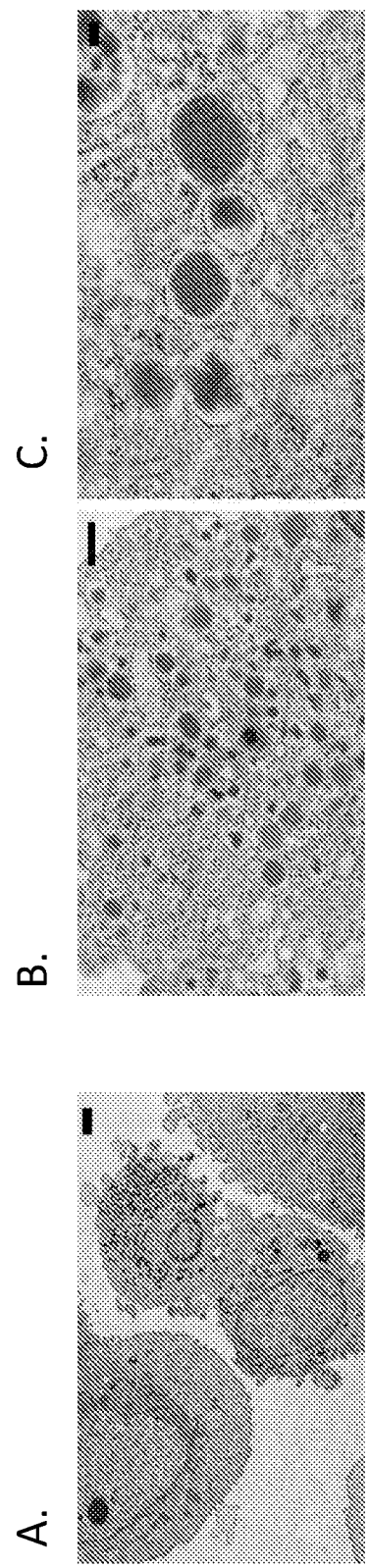

FIG. 13. Representative electron microscopic images of cells reprogrammed with siARX. Unlike non reprogrammed cells, reprogrammed cells are rich in dense secretory granules (A). Scale bar=2 µm. High magnification images (B and C) of dense core vesicles with different morphologies in reprogrammed cells. Scale bar=0.5 µm (B) and 0.1 µm (C).

Figure 14:
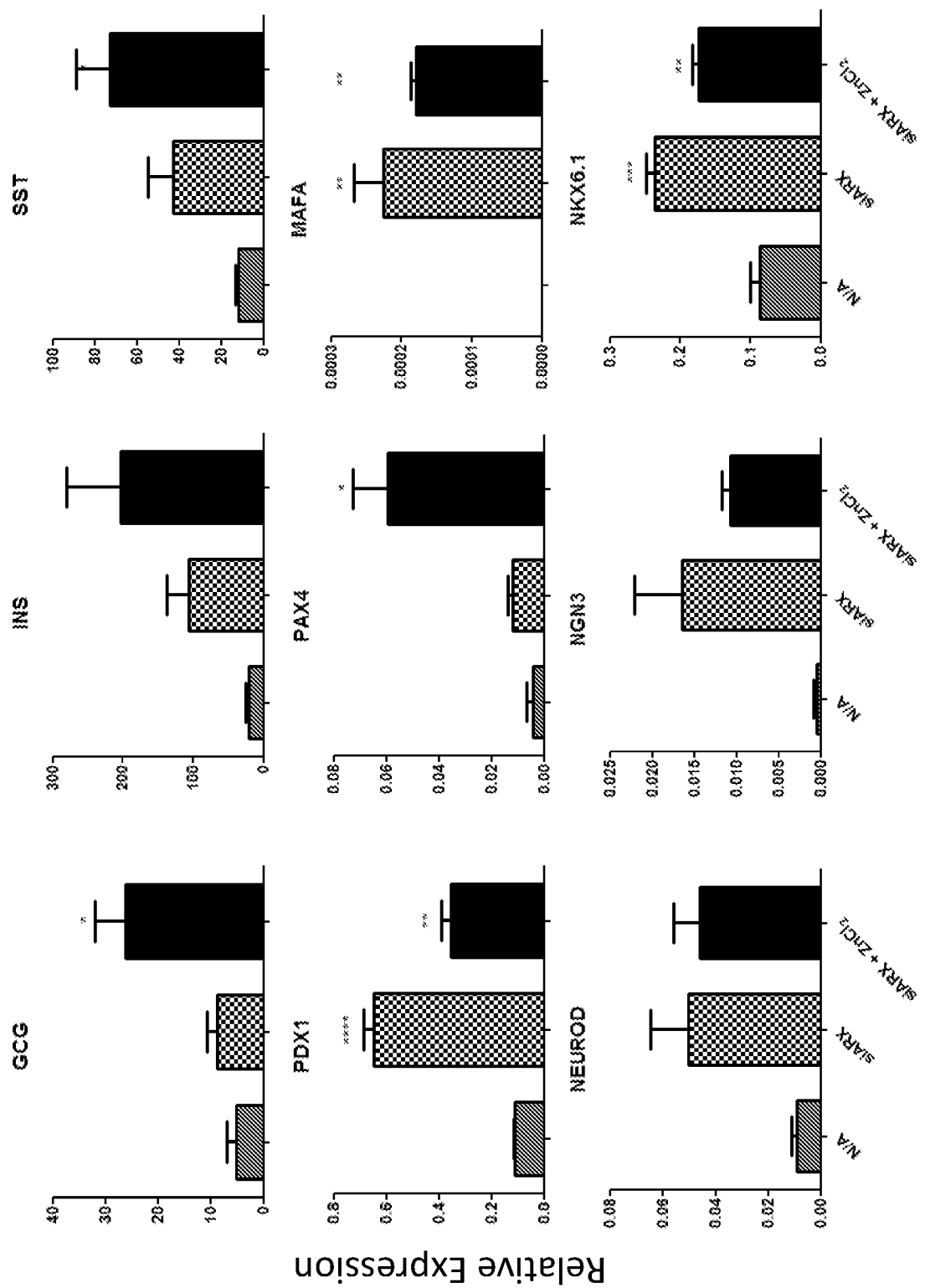

FIG. 14. RT-qPCR analysis of the three main endocrine hormones insulin (INS), glucagon (GCG) and somatostatin (SST) and the transcription factors PDX1, PAX4, MAFA, NEUROD, NGN3 and NKX6.1 in untreated (N/A) or cells reprogrammed (siARX) in the absence or presence of $ZnCl_2$ (10 µM). Expression was normalised to glyceraldehyde 3-phosphate dehydrogenase. Data are representative of triplicate experiments and represented as mean+/−standard error of the mean.

Figure 15:
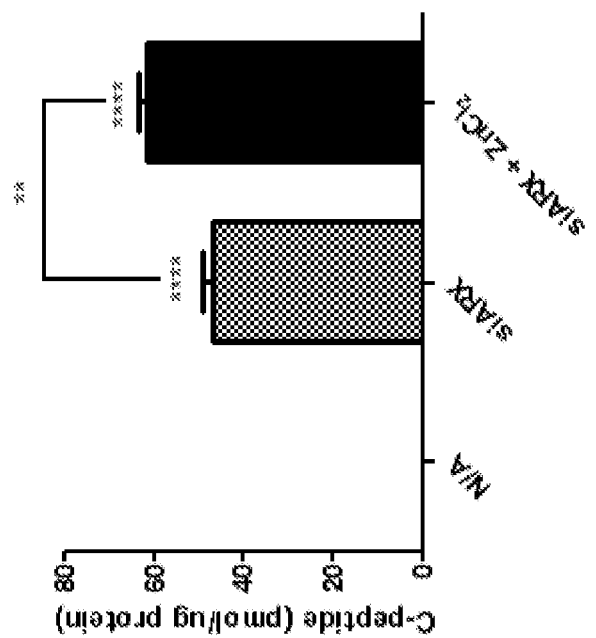

FIG. 15. C-peptide ELISA measurements of cell extracts from untreated cells (N/A) or cells reprogrammed (siARX) in the absence or presence of $ZnCl_2$ (10 µM). C-peptide levels were expressed level to protein content and represent 3±SD (n=3). *$p<0.001$ relative to NA and $p<0.01$ relative to siARX.

EXAMPLES

Example 1

Materials and Methods

Culture of Human Exocrine Pancreatic Fractions.

All human tissue was procured with appropriate ethical consent. Human pancreata (n=42) were isolated from brain-dead adult donors in the Scottish Islet Isolation Laboratory (SNBTS, Edinburgh, UK). The mean donor age was 39.4 years (range 23-61 years) and BMI 27.2 kg/m2 (range 22-36.5 kg/m2).

Culture where EMT is Inhibited.

Following islet isolation the low purity exocrine fractions were transported to Aberdeen where the cells were immediately cryopreserved in liquid nitrogen at a density of 300,000 exocrine clusters per vial. The cells were cryopreserved in 90% fetal bovine serum (FBS, Gibco, Life Technologies, Paisley, UK) and 10% DMSO (Sigma Aldrich, Dorset, UK). Human exocrine fractions were thawed and plated on tissue culture 9 cm² dishes (Greiner, Stonehouse, UK) and cultured for two days in RPMI 1640 (Gibco, Life Technologies) supplemented with 10% foetal bovine serum (FBS), 10 mM HEPES, 1 mM sodium pyruvate (all from Gibco) and 75 µM β-mercaptoethanol (Sigma Aldrich).

After 48 h the cells were incubated for another 72 h in serum free medium (SFM) prepared with RPMI 1640, insulin-transferrin-selenium (Gibco) and 1% bovine serum albumin (Sigma), supplemented with 10 µM SB431542, 2 µM Y27632, 1 µM 5-Aza-2'deoxycytidine and 10 mM sodium butyrate (all from Sigma). On the next day the cells were incubated for 4 h with the adenoviruses encoding pancreatic transcription factors. On the following day the medium was changed for SFM supplemented with 1 nM betacellulin (R&D systems, Abingdon, UK), 10 nM exendin-4 and 10 mM nicotinamide (both from Sigma). The medium was changed every two days for another 6 days before harvesting.

Culture to Obtain MSCs for Reprogramming where EMT is not Inhibited.

Following islet isolation for clinical application the low purity exocrine fractions were transported to Aberdeen where the cells were immediately plated at a density of 300,000 exocrine clusters on 75 cm² tissue culture flask (Greiner, Stonehouse, UK) and cultured in serum complete medium (SCM) prepared using RPMI 1640 (Gibco, Life Technologies, Paisley, UK) supplemented with 10% foetal bovine serum (FBS), 10 mM HEPES, 1 mM sodium pyruvate (all from Gibco) and 75 µM β-mercaptoethanol (Sigma Aldrich, Dorset, UK).

Human exocrine pancreatic cells were passaged every 7 days with a solution of Trypsin (0.05%)-EDTA (0.02%, Gibco). Serum free medium (SFM) was prepared using RPMI 1640 supplemented with 1% bovine serum albumin (BSA, Sigma), 10 µg/ml insulin and 5.5 µg/ml transferrin (both from Roche Diagnostics, West Sussex, UK).

Preparation of Adenoviruses.

Recombinant adenoviruses encoding the mouse sequences of PDX1, MAFA, NGN3 and PAX4 (Swales et al., 2012) were prepared using the Ad-Easy™ system (Agilent Technologies, Edinburgh, UK). The adenoviruses containing PDX1 and NGN3 also expressed GFP through a downstream CMV promoter. Viral transduction was performed in SFM for 4 h at a multiplicity of infection (MOI) of 100 for each virus.

Quantitative Reverse Transcription Polymerase Chain Reaction (qRT-PCR).

QRT/PCR was performed as previously described (Lima et al., 2012. Data were analysed using the $2^{-\Delta\Delta CT}$ method. Statistical analysis was performed using PRISM software and the student's t-test or one-way ANOVA followed by the Dunnet's post-hoc test, as appropriate. The list of TaqMan probes are listed in Table 1:

TABLE 1

List of Taqman ® gene expression primers:

| Gene | Assay ID |
|---|---|
| GAPDH | Hs99999905_m1 |
| INS | Hs00355773_m1 |
| GCG | Hs00174967_m1 |
| SST | Hs001174949_m1 |
| PDX1 | Hs00236830_m1 |
| NGN3 | Hs01875204_s1 |
| MAFA | Hs01651425_s1 |
| NKX6.1 | Hs00232355_m1 |
| NEUROD1 | Hs00159598_m1 |
| PAX6 | Hs00240871_m1 |

Immunocytochemistry and Immunohistochemistry.

Immunocytochemistry and immunohistochemistry were performed as previously described (Cho, C-H, Hannan, N, Docherty, F M., Docherty, H M. Docherty, K. Vallier L.; Lima et al., 2012, using the antibodies listed in Table 2:

TABLE 2 antibodies used in immunohistochemistry and immunocytochemistry

| Antigen | Antibody host | Source | Dilution used |
|---|---|---|---|
| C-peptide | Mouse | Cell Signalling | 1:1000 |
| Glucagon | Mouse | Sigma | 1:1000 |

C-Peptide Release Studies.

C-peptide levels were measured using a human glucagon Quantikine ELISA kit (R&D Systems, Abingdon, UK), a human C-peptide ELISA kit (Millipore, Livingston, UK), a human prosinsulin ELISA kit or a human insulin ELISA kit (both from Mercodia, Uppsala, Sweden).

siRNA Based Knockdown.

Knockdown of Arx in transdifferentiating cells was performed by transfection with a pool of specific targeting small inhibitory RNAs, or scrambled controls (Dharmacon, Loughborough, UK). 100 nM siRNA was transfected on day 6 of the transdifferentiation protocol using Dharmafect 1 (Dharmacon), according to the manufacturer's instructions.

Results

Combinations of Transcription Factors (TFs) Induce Reprogramming of Human Exocrine Enriched Fraction (EEF).

We examined various combinations of 6 pancreatic transcription factors (TFs), namely PDX1, MAFA, PAX4, NGN3, NKX6.1 and NeuroD1 in our previously published (Lima et al., 2013) reprogramming protocol. The difference in insulin expression observed between mature islets and transdifferentiated cells suggested that the latter had not reached the same maturation status as adult islets. In order to improve the transdifferentiation outcome, thirty different combinations of pancreatic TFs were tested (FIG. 1C). Expression of insulin (FIG. 1A), glucagon and somatostatin (FIG. 9) was measured.

EEF cells were plated directly from the low purity fractions obtained following islet isolation. EEF cells were cultured as a monolayer for two days and then treated with SB, Y2, Aza and NaBu for 3 days. The cells were then transduced with various combinations of adenoviruses containing TFs (AD-TFs) as indicated in FIG. 1A and further cultured in presence of betacellulin, exendin-4 and nicotinamide (BEN) for 6 days.

Of the 29 combinations, 4 provided significant levels of insulin gene expression (combinations 20, 24, 25 and 29 in FIG. 1). All four combinations increased the level of endogenous TFs suggesting that reprogramming or transdifferentiation was taking place (FIG. 2).

Condition 1 is untreated cells.

Condition 30 is cells treated with soluble factors (SFs) in absence of Ad-TFs.

Condition 20 is cells treated with PDX1/NGN3/NKX6.1/NeuroD1

Condition 24 is cells treated with PDX1/MAFA/NKX6.1/NeuroD1

Condition 25 is cells treated with PDX1/MAFA/NGN3/NeuroD1

Condition 29 is cells treated with PDX1/MAFA/NGN3/PAX4

RT-qPCR analysis was used to monitor expression of the endocrine hormones insulin, glucagon and somatostatin relative to glyceraldehyde 3-phosphate dehydrogenase. The combinations after treatment with each transcription factor combination shown in FIG. 1C. There seems to be a preference for addition of NKX6.1 for reprogramming to glucagon-expressing alpha cells and of NeuroD1 for reprogramming to somatostatin-expressing delta cells (FIG. 9)

The cells in this experiment may be reprogrammed to endocrine cells directly from exocrine cells without fully entering a mesenchymal state. Although the process of attaching to the culture may initiate the epithelial to mesenchymal transition (EMT), in these experiments the cells where attached for only a limited period (~48 h) before inhibition of EMT. Thus in these experiments the processes that further establish and sustain the EMT were generally inhibited or supressed.

PAX4 is Essential for the Generation of Glucose Sensitive β-Cells

Of the combinations, only combination 29 was able to regenerate cells that secreted insulin (C-peptide) in response to glucose (FIG. 3). This is the only combination of the four that contains PAX4.

Therefore, although similar levels of insulin expression were obtained when replacing PAX4 by either NKX6.1 or NeuroD, only in the presence of PAX4 were the transdifferentiated cells able to secrete insulin in a glucose dependent manner, indicating that PAX4 plays a crucial role in establishing the functionality of mature beta cells in humans.

RT-QPCR of late beta cell markers further demonstrated that MAFA expression was only present in cells transdifferentiated with the combination 29 (PDX1/MAFA/NGN3/PAX4, also named the '4TF combination') (FIG. 2), indicating that its expression is a key factor for beta cell functionality. This leads to the conclusion that inclusion of PAX4 is essential for the generation of glucose sensitive β-cells.

Growth on Laminin-Coated Plates Improves the Efficiency of Reprogramming

We next compared the effect of extracellular matrices on the efficiency of the reprogramming protocol using PDX1/MAFA/NGN3/PAX4. Laminin, fibronectin, poly-lysine, collagen type I and collagen type IV were compared and the relative expression of insulin was assessed (FIG. 4). The results show that growth on laminin-coated plated improves the efficiency of reprogramming.

Culture in Media Containing Low Concentrations of Glucose Further Enhances Reprogramming Towards β-Cells Cells were cultured in different concentrations of glucose, and the relative expression of insulin is shown in FIG. 5. The results show that culture in media containing low concentrations of glucose further enhances reprogramming of EEFs towards insulin-expressing β-cells. Glucose was added to SFM and cells were cultured with glucose for 10 days.

Knock-Down of Endogenous Transcription Factor (TF) ARX in the Presence of Exogenous PAX4 Enhances the Efficiency of Reprogramming Towards β-Cells EEF cells were cultured as a monolayer for two days and then treated with SB, Y2, Aza and NaBu for 3 days. The cells were then transduced with PDX1/MAFA/NGN3/PAX4 (REP') or PDX1/MAFA/NGN3 ('-PAX4') and further cultured in presence of BEN for 6 days. Silencing of endogenous transcription factor (TF) ARX by siRNA was carried out at day 6 post addition of SB, Y2, Aza and NaBu (FIG. 6A) and the results are shown in FIGS. 6B, C and D. ARX silencing in the presence but not in the absence of exogenous Pax4 clearly stimulates INS (FIG. 6B) and SST (FIG. 6C) production but has no effect on GCG expression (FIG. 6D).

ARX expression was inhibited by siRNA at the late stages of the reprogramming protocol, resulting in a ~100 fold increase in insulin expression levels (FIG. 6B). Accordingly, ARX inhibition has led to an enhanced release of C-peptide by the reprogrammed cells in response to a high glucose concentration in vitro (FIG. 7). Reprogrammed islets express insulin at levels around 15% of that in adult human islets (FIG. 8).

Moreover, removal of PAX4 from the reprogramming cocktail has abolished C-peptide release in response to high glucose levels, indicating that the action of PAX4 is essential for the functionality and maturation of the reprogrammed beta-cells. These studies indicate that the regulatory loop between ARX and PAX4 during the final stages of pancreatic development is essential for the functionality of human beta cells generated in vitro. These experiments show that knock-down of endogenous ARX in the presence of exogenous PAX4 enhances the efficiency of reprogramming.

ARX expression was inhibited by siRNA at the late stages of the transdifferentiation protocol, resulting in a ~60 fold increase in insulin expression levels compared to cells treated with control siRNA, bringing insulin expression levels much closer to those of mature beta cells (FIG. 10B). Further, reprogrammed islets (where ARX expression was inhibited) were shown to process proinsulin in a manner similar to that of adult human islets as evidenced by ELISA data using antibodies specific to proinsulin, insulin and C-peptide. (FIG. 10B)

Cells reprogrammed in the absence of ARX inhibition (Lima et al. 2013) express only 1% of the insulin levels found in mature adult islets. These cells are labelled REP in FIG. 10B).

ARX Inhibition Enhances Beta Cell Maturation and Decreases Alpha Cell Differentiation RT-QPCR has shown that ARX is expressed during the differentiation protocol and may favour the development of alpha versus beta cells during reprogramming of the exocrine derived material.

Glucagon protein levels were significantly down-regulated after inhibition of ARX expression (FIG. 10O). Specific ELISAs for human insulin and C-Peptide demonstrated that the transdifferentiated cells were able to efficiently store and process insulin, secreting C-peptide in a regulated glucose-responsive manner, with levels comparable to those found in human islets (FIG. 10). To further support its role in the functionality and maturation of the reprogrammed beta cells, removal of PAX4 from the transdifferentiation protocol resulted in the abolishment of C-peptide release in response to an increased glucose concentration. (FIG. 10A).

Reprogrammed Insulin Producing Cells Prevent STZ-Induced Diabetes In Vivo.

The in vivo function of the reprogrammed insulin producing cells was further determined by transplanting these cells under the kidney capsule of NOD/SCID mice that had been rendered diabetic with STZ 1 day before surgery (FIG. 11A).

The cells used were from exocrine enriched tissue that had been plated in SFM and treated with SB431542, Y27632, 5-Aza-2'deoxycytidine, sodium butyrate, 4TF and BEN (no ARX inhibitor).

Animals that were transplanted with reprogrammed cells retained normal blood glucose levels and maintained body weight throughout the course of the experiment. Animals that were transplanted with non-reprogrammed exocrine cells, or those that were not transplanted with cells under the kidney capsule, exhibited markedly elevated blood glucose levels associated with weight loss (FIG. 11A).

Removal of the transplanted kidney after 30 days resulted in an increase in the blood glucose levels of the animals transplanted with the reprogrammed cells (FIG. 11A). Human C-peptide was present only in the serum of fed mice that were transplanted with the reprogrammed insulin-producing cells (FIG. 11 B) but was absent from the blood when fasted, suggesting that the reprogrammed cells released insulin in a glucose-responsive manner in vivo. Immunostaining of the grafted kidneys showed that the transplanted cells formed a cluster-like structure under the kidney capsule, where the centre of the structure was mainly composed of strongly positive insulin positive cells, with the majority of the glucagon-positive cells localized in the periphery of the cluster (FIG. 11C). The majority of the cells in this structure also were positive for the pancreatic TF Pdx1 (FIG. 11D). Collectively, these data support the conclusion that the exocrine pancreatic cells of the adult human pancreas can be reprogrammed toward functional insulin-producing cells. The reprogrammed cells are able to ameliorate diabetes in a diabetic mouse model and generate a cluster-like structure reminiscent of islets of Langerhans.

Transdifferentiated Pancreatic Mesenchymal Stem Cells (MSCs) were Shown to Release Glucagon in a Regulated Manner In Vivo.

NOD/SCID were mice grafted with cells reprogrammed using A+Bu+4TFs+BEN (inhibitors of EMT were not used), and non grafted mice were used as a control. Glucagon was measured from the serum of grafted animals after a 4 h starvation period (fast) or under ad libitum feeding (fed) conditions, and was shown to present at a higher concentration in mice grated with treated cells.

The NOD/SCID mice were rendered diabetic with one dose of streptozotocin, one day prior to surgery. Glucagon was measured from the serum of grafted animals after a 4 h starvation period (fast) or under ad libitum feeding (fed) conditions, and was shown to be present at a higher concentration in the fasting mice.

The data show that the treated pancreatic mesenchymal stem cells (MSCs) released glucagon in a regulated manner in vivo.

Example 2

Methods

Reprogramming of Human Exocrine Pancreatic Fractions

Human exocrine fractions were thawed and plated on tissue culture 9 cm$^2$ dishes (Greiner, Stonehouse, UK) and cultured for two days in RPMI 1640 (Gibco, Life Technologies) supplemented with 10% foetal bovine serum (FBS), 10 mM HEPES, 1 mM sodium pyruvate (all from Gibco) and 75 µM β-mercaptoethanol (Sigma Aldrich). After 48 h, the cells were incubated for another 72 h in serum free medium (SFM) prepared with RPMI 1640, insulin-transferrin-selenium (Gibco) and 1% bovine serum albumin (Sigma), supplemented with 10 µM SB431542, 2 µM Y27632, 1 µM 5-Aza-2'deoxycytidine and 10 mM sodium butyrate (all from Sigma). On the next day the cells were incubated for 4 h with the adenoviruses encoding pancreatic transcription factors PDX1, MAFA, NGN3 and PAX4. On the following day the medium was changed for SFM supplemented with 1 nM betacellulin (R&D systems, Abingdon, UK), 10 nM exendin-4 and 10 mM nicotinamide (both from Sigma). The medium was changed every two days for another 6 days before harvesting.

Knockdown of ARX was performed by transfection with a pool of specific targeting small inhibitory RNAs, or scrambled controls (all from Dharmacon, Loughborough, UK). siRNA (100 nM) transfected on day 6 of the reprogramming protocol using Dharmafect 1 (Dharmacon), according to the manufacturer's instructions. ZnCl$_2$ was used at a concentration of 10 µM and was used in combination with the reprogramming adenoviruses and the siARX.

Transmission Electron Microscopy

Cells were detached from plates using Accutase™ (BD Biosciences, Oxford, UK) and subsequently fixed in 2.5% glutaraldehyde in 0.1M sodium cacodylate buffer at 4° C. overnight. The cells were subsequently post-fixed with 1% osmium tetroxide for 1 h followed by embedding in epoxy resin. The samples were then dehydrated in a series of ethanol washes for 20 min each starting at 70%, 95% and 100%. The samples were then embedded in epoxy resin, placed into moulds, and left to polymerise at 65° C. for 48 h. Sections were taken between 75 and 90 nm on a Leica Ultracut E (Leica, Wetzlar, Germany) and placed on formvarlcarbon coated slot grids. Images were observed on a JEOL JEM-1400 Plus TEM, and captured using an AMT UltraVue camera (Woburn, Mass., USA).

Results

Electron microscopy of human exocrine cells reprogrammed according to the protocol containing siARX revealed the presence of dense core granules that were polarised towards one side of the cell (FIG. 13A), a pattern that is typical of islet beta cells.

Higher magnification (FIGS. 13B and 13C) showed the presence of granules, with in some instances a clear dense core surrounded by a non-opaque halo, properties that are characteristic of insulin secretory granules. The dense core of these granules is due to the presence of insulin-zinc hexameric crystalline structures. However, there were also granules that had a less dense core and lacked a halo.

It was hypothesised that the lack of zinc in the media could contribute to these intermediate granule forms. This suggested that inclusion of zinc in the media would not only lead to the formation of more dense core secretory granules, but would also enhance the insulin secretory response to glucose and the insulin content of the reprogrammed cells.

Zinc Increases the Level of Insulin mRNA in Reprogramed Cells, Possibly Through a Mechanism that Involves PAX4

To test this hypothesis cells were reprogrammed in the presence or absence of zinc and analysed by RT/QPCR. Cells were reprogrammed (siARX) using the transcription factors and siARX as set out under 'Methods'. The results demonstrated a significant effect of zinc on insulin gene expression that could in part be attributed to increased levels of mRNA encoding PAX4 (FIG. 14).

Zinc Increases the Insulin (C-Peptide) Content of the Reprogrammed Cells

Further studies showed that Zinc ($ZnCl_2$) had a stimulatory effect on the insulin (C-peptide) protein content of the reprogrammed (siARX) cells (FIG. 15).

REFERENCES

Akinci, E., Banga, A., Greder, L. V., Dutton, J. R., and Slack, J. M. (2012). Reprogramming of pancreatic exocrine cells towards a beta (beta) cell character using PDX1, NGN3 and MAFA. Biochem. J. 442, 539-550.

Alipio, Z., Liao, W., Roemer, E. J., Waner, M., Fink, L. M., Ward, D. C., and Ma, Y. (2010). Reversal of hyperglycemia in diabetic mouse models using induced-pluripotent stem (iPS)-derived pancreatic beta-like cells. Proc. Natl. Acad. Sci. U.S.A 107, 13426-13431.

Baeyens, L., De Breuck, S., Lardon, J., Mfopou, J. K., Rooman, I., and Bouwens, L. (2005). In vitro generation of insulin-producing beta cells from adult exocrine pancreatic cells. Diabetologia 48, 49-57.

Bar, Y., Russ, H. A., Sintov, E., Anker-Kitai, L., Knoller, S., and Efrat, S. (2012). Redifferentiation of Expanded Human Pancreatic beta-Cell-derived Cells by Inhibition of the NOTCH Pathway. J. Biol. Chem. 287, 17269-17280.

Blum, B., Hrvatin, S. S., Schuetz, C., Bonal, C., Rezania, A., and Melton, D. A. (2012). Functional beta-cell maturation is marked by an increased glucose threshold and by expression of urocortin 3. Nat. Biotechnol. 30, 261-264.

Chandra, V., Swetha, G., Muthyala, S., Jaiswal, A. K., Bellare, J. R., Nair, P. D., and Bhonde, R. R. (2011). Islet-like cell aggregates generated from human adipose tissue derived stem cells ameliorate experimental diabetes in mice. PLoS One 6, e20615.

Cho, C-H, Hannan, N, Docherty, F M., Docherty, H M. Docherty, K. Vallier L. Activin/TGFb signalling pathway controls hepatic and pancreatic specification of human endoderm.

Collombat, P., Mansouri, A., Hecksher-Sorensen, J., Serup, P., Krull, J., Gradwohl, G., and Gruss, P. (2003). Opposing actions of ARX and PAX4 in endocrine pancreas development. Genes Dev. 17, 2591-2603.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat. Biotechnol. 24, 1392-1401.

Davani, B., Ikonomou, L., Raaka, B. M., Geras-Raaka, E., Morton, R. A., Marcus-Samuels, B., and Gershengorn, M. C. (2007). Human islet-derived precursor cells are mesenchymal stromal cells that differentiate and mature to hormone-expressing cells in vivo. Stem Cells 25, 3215-3222.

Docherty, K. (2011). Reprogramming Toward Pancreas Beta Cells. Stem Cell Biology and Regenerative Medicine Docherty, K., Bernardo, A. S., and Vallier, L. (2007). Embryonic stem cell therapy for diabetes mellitus. Semin. Cell Dev. Biol. 18, 827-838.

Ferber, S., Halkin, A., Cohen, H., Ber, I., Einav, Y., Goldberg, I., Barshack, I., Seijffers, R., Kopolovic, J., Kaiser, N., and Karasik, A. (2000). Pancreatic and duodenal homeobox gene 1 induces expression of insulin genes in liver and ameliorates streptozotocin-induced hyperglycemia 6. Nat. Med. 6, 568-572.

Gershengorn, M. C., Hardikar, A. A., Wei, C., Geras-Raaka, E., Marcus-Samuels, B., and Raaka, B. M. (2004). Epithelial-to-mesenchymal transition generates proliferative human islet precursor cells. Science 306, 2261-2264.

Hao, E., Tyrberg, B., Itkin-Ansari, P., Lakey, J. R., Geron, I., Monosov, E. Z., Barcova, M., Mercola, M., and Levine, F. (2006). Beta-cell differentiation from nonendocrine epithelial cells of the adult human pancreas. Nat. Med. 12, 310-316.

Jiang, J., Au, M., Lu, K., Eshpeter, A., Korbutt, G., Fisk, G., and Majumdar, A. S. (2007). Generation of insulin-producing islet-like clusters from human embryonic stem cells. Stem Cells 25, 1940-1953.

Jiang, W., Shi, Y., Zhao, D., Chen, S., Yong, J., Zhang, J., Qing, T., Sun, X., Zhang, P., Ding, M., Li, D., and Deng, H. (2007). In vitro derivation of functional insulin-producing cells from human embryonic stem cells. Cell Res. 17, 333-344.

Karnieli, O., Izhar-Prato, Y., Bulvik, S., and Efrat, S. (2007). Generation of insulin-producing cells from human bone marrow mesenchymal stem cells by genetic manipulation. Stem Cells 25, 2837-2844.

Kojima, H., Fujimiya, M., Matsumura, K., Younan, P., Imaeda, H., Maeda, M., and Chan, L. (2003). NeuroD-betacellulin gene therapy induces islet neogenesis in the liver and reverses diabetes in mice. Nat. Med. 9, 596-603.

Kroon, E., Martinson, L. A., Kadoya, K., Bang, A. G., Kelly, O. G., Eliazer, S., Young, H., Richardson, M., Smart, N. G., Cunningham, J., et al. (2008). Pancreatic endoderm derived from human embryonic stem cells generates glucose-responsive insulin-secreting cells in vivo. Nat. Biotechnol. 26, 443-452.

Lima, M. J., Docherty, H. M., Chen, Y., and Docherty, K. (2012). Efficient differentiation of AR42J cells towards insulin-producing cells using pancreatic transcription factors in combination with growth factors. Mol. Cell. Endocrinol. 358, 69-80.

Lima, M. J., Muir, K. R., Docherty, H. M., Drummond, R., McGowan, N. W., Forbes, S., Heremans, Y., Houbracken, I., Ross, J. A., Forbes, S. J., et al. (2013). Suppression of epithelial-to-mesenchymal transitioning enhances ex vivo reprogramming of human exocrine pancreatic tissue toward functional insulin-producing beta-like cells. Diabetes 62, 2821-2833.

Montgomery, A. M., and Yebra, M. (2011). The Epithelial-to-Mesenchymal Transition of Human Pancreatic beta Cells: Inductive Mechanisms and Implications for the Cell-Based Therapy of Type I Diabetes. Curr. Diabetes Rev.

Ogihara, T., Fujitani, Y., Uchida, T., Kanno, R., Choi, J. B., Hirose, T., Kawamori, R., and Watada, H. (2008). Combined expression of transcription factors induces AR42J-B13 cells to differentiate into insulin-producing cells. Endocr. J. 55, 691-698.

Ouziel-Yahalom, L., Zalzman, M., Anker-Kitai, L., Knoller, S., Bar, Y., Glandt, M., Herold, K., and Efrat, S. (2006). Expansion and redifferentiation of adult human pancreatic islet cells. Biochem. Biophys. Res. Commun. 341, 291-298.

Porat, S., Weinberg-Corem, N., Tornovsky-Babaey, S., Schyr-Ben-Haroush, R., Hija, A., Stolovich-Rain, M., Dadon, D., Granot, Z., Ben-Hur, V., White, P., et al. (2011). Control of pancreatic beta cell regeneration by glucose metabolism. Cell. Metab. 13, 440-449.

Rezania, A., Bruin, J. E., Riedel, M. J., Mojibian, M., Asadi, A., Xu, J., Gauvin, R., Narayan, K., Karanu, F., O'Neil, J. J., et al. (2012). Maturation of Human Embryonic Stem Cell-Derived Pancreatic Progenitors into Functional Islets Capable of Treating Pre-existing Diabetes in Mice. Diabetes Rezania, A., Riedel, M. J., Wideman, R. D., Karanu, F., Ao, Z., Warnock, G. L., and Kieffer, T. J. (2011). Production of functional glucagon-secreting alpha-cells from human embryonic stem cells. Diabetes 60, 239-247.

Schulz, T. C., Young, H. Y., Agulnick, A. D., Babin, M. J., Baetge, E. E., Bang, A. G., Bhoumik, A., Cepa, I., Cesario, R. M., Haakmeester, C., et al. (2012). A scalable system for production of functional pancreatic progenitors from human embryonic stem cells. PLoS One 7, e37004.

Shapiro, A. M., Lakey, J. R., Ryan, E. A., Korbutt, G. S., Toth, E., Warnock, G. L., Kneteman, N. M., and Rajotte, R. V. (2000). Islet transplantation in seven patients with type 1 diabetes mellitus using a glucocorticoid-free immunosuppressive regimen 4. N. Engl. J. Med. 343, 230-238.

Swales, N., Martens, G. A., Bonne, S., Heremans, Y., Borup, R., Van de Casteele, M., Ling, Z., Pipeleers, D., Ravassard, P., Nielsen, F., Ferrer, J., and Heimberg, H. (2012). Plasticity of adult human pancreatic duct cells by neurogenin3-mediated reprogramming. PLoS One 7, e37055.

Tateishi, K., He, J., Taranova, O., Liang, G., D'Alessio, A. C., and Zhang, Y. (2008). Generation of insulin-secreting islet-like clusters from human skin fibroblasts. J. Biol. Chem. 283, 31601-31607.

Wang, H. S., Shyu, J. F., Shen, W. S., Hsu, H. C., Chi, T. C., Chen, C. P., Huang, S. W., Shyr, Y. M., Tang, K. T., and Chen, T. H. (2011). Transplantation of insulin-producing cells derived from umbilical cord stromal mesenchymal stem cells to treat NOD mice. Cell Transplant. 20, 455-466.

Yechoor, V., Liu, V., Espiritu, C., Paul, A., Oka, K., Kojima, H., and Chan, L. (2009). Neurogenin3 is sufficient for transdetermination of hepatic progenitor cells into neo-islets in vivo but not transdifferentiation of hepatocytes. Dev. Cell. 16, 358-373.

Zhang, T., Saunee, N. A., Breslin, M. B., Song, K., and Lan, M. S. (2012). Functional role of an islet transcription factor, INSM1/1A-1, on pancreatic acinar cell trans-differentiation. J. Cell. Physiol. 227, 2470-2479.

Zhou, Q., Brown, J., Kanarek, A., Rajagopal, J., and Melton, D. A. (2008). In vivo reprogramming of adult pancreatic exocrine cells to beta-cells. Nature

The invention claimed is:

1. A method for ex-vivo reprogramming comprising:
   a) providing pancreatic cells to be reprogrammed,
   b) reprogramming the pancreatic cells, comprising:
      (i) treating the pancreatic cells with PAX4, PDX1, MAFA and NGN3 transcription factors and
      (ii) inhibiting ARX expression and/or function
   c) thereby obtaining beta-like cells that express insulin mRNA.

2. The method according to claim 1, wherein the beta-like cells obtained in step (c) are capable of producing insulin protein in response to glucose stimulation.

3. The method according to claim 1, wherein the beta-like cells obtained in step (c) produce insulin protein at a level of at least 5% of that of adult human islets.

4. The method according to claim 1, wherein ARX expression is inhibited.

5. The method according to claim 4, wherein ARX expression is inhibited using RNA interference (RNAi).

6. The method according to claim 4, wherein ARX expression is inhibited by siRNA.

7. The method according to claim 1, wherein the cells are cultured on laminin throughout the method, or
   wherein during the reprogramming the cells are cultured in glucose, wherein the glucose concentration is between 0-5 mM, or
   wherein the cells are cultured in adherent culture prior to reprogramming, optionally for about 2 days, or
   a combination thereof.

8. The method according to claim 1, wherein the pancreatic cells provided in step (a) are human pancreatic cells, or
   wherein the pancreatic cells provided in step (a) comprise exocrine cells, optionally from an exocrine enriched fraction of a pancreas, or
   a combination thereof.

9. The method according to claim 1, wherein the
   reprogramming further comprises the step of pre-treating the cells, before treatment with the one or more transcription factors, with an inhibitor of epithelial to mesenchymal transition, or
   reprogramming further comprises the step of pre-treating the cells, before treatment with the one or more transcription factors, with a chromatin modifying agent, or
   a combination thereof.

10. The method according to claim 9, wherein the inhibitor of epithelial to mesenchymal transition is a TGFbetal signaling pathway inhibitor, a Rho-associated protein kinase (Rock) signaling pathway inhibitor, or a combination thereof.

11. The method according to claim 9, wherein the chromatin-modifying agent is a DNA-methyltransferase inhibitor, a histone deacetylase (HDAC) inhibitor, or a combination thereof.

12. The method according to claim 1, further comprising culturing the cells in media comprising betacellulin, exendin-4, nicotinamide, or a combination thereof.

13. The method according to claim 1, wherein the reprogramming comprises treatment with zinc.

* * * * *